United States Patent [19]

Klein et al.

[11] Patent Number: 5,358,868
[45] Date of Patent: * Oct. 25, 1994

[54] GENETIC DETOXIFICATION OF PERTUSSIS TOXIN

[75] Inventors: Michel H. Klein, Willowdale; Heather A. Boux, Aurora; Stephen A. Cockle, Richmond Hill; Sheena M. Loosmore, Aurora; Gavin R. Zealey, Concord, all of Canada

[73] Assignee: Connaught Laboratories Limited, Willowdale, Canada

[ * ] Notice: The portion of the term of this patent subsequent to Jun. 22, 2010 has been disclaimed.

[21] Appl. No.: 788,313

[22] Filed: Nov. 5, 1991

Related U.S. Application Data

[60] Division of Ser. No. 589,423, Sep. 28, 1990, Pat. No. 5,244,657, which is a continuation-in-part of Ser. No. 275,376, Nov. 23, 1988, Pat. No. 5,085,862.

[30] Foreign Application Priority Data

Nov. 24, 1987 [GB] United Kingdom ............... 8727489

[51] Int. Cl.$^5$ .............. C12N 1/00; C12N 15/00; C12N 1/12; C07K 3/00
[52] U.S. Cl. ............... 435/243; 435/172.1; 435/252.1; 435/172.3; 536/23.5; 536/23.1; 530/324; 530/350
[58] Field of Search ............ 435/69.1, 69.3, 252.1, 435/172.1, 172.2, 172.3, 243; 536/27, 23.5; 935/10, 11, 12, 65; 530/324, 350

[56] References Cited

FOREIGN PATENT DOCUMENTS 0275689 7/1988 European Pat. Off. .
0322533 3/1989 European Pat. Off. .
0306318 3/1990 European Pat. Off. .

OTHER PUBLICATIONS

Moss et al., J. Biol. Chem. 258, 11879 [1983].
Locht and Keith, Science 232, 1258 [1986].
Carrol & Collier, Proc. Nat. Acad. Sci., U.S.A., 81, 3307 [1984].
Carroll & Collier, J. Biol. Chem., 262, 8707 [1987].
Nogimori et al, Biochem., 25, 1355 [1986].
Armstrong & Peppler, Infec. Immun., 55, 1294 [1987].
Tweten et al., J. Biol. Chem., 260, 10392 [1984].
Douglas & Collier, J. Bacteriol., 169, 4967, [1987].
Locht et al., Infect. Immun., 55, 4967, [1987].
Black et al., Ann. Sclavo, 175, [1986].
Black & Falkow, Infect. Immum., 55, 2465, [1987].
Burns et al., Infect. Immun., 55, 24, [1987].
Watkins et al., J. Biol. Chem. 260, 13478, [1985].
Ditta et al., Plasmid, 13, 149, [1985].
Kahn et al., Methods in Enzymology, 68, 278, [1979]*.
Nicosia et al, Proc. Nat. Acad. Sci., U.S.A., 83, 4631, [1986].
Arico & Rappuoli, J. Bacteriol., 169, 2849, [1987], Gene, vol. 50, 1986, pp. 133–140; Elsevier.
S. Stibitz et al.: "The Construction of a cloning vector designed for gene replacement in Bordetella pertussis"; Biochemistry, vol. 21, 1982, pp. 5516–5522, American Chemical Society.
M. Tamura et al.: "Subunit structure of islet-activating protein, pertussis toxin, in conformity with the A-B mode".
Chemical Abstracts, vol. 105, No. 19, Nov. 10, 1986, ref. No. 166239w: Columbus, Ohio. US.

(List continued on next page.)

Primary Examiner—Robert J. Hill, Jr.
Assistant Examiner—Gian P. Wang
Attorney, Agent, or Firm—Sim & McBurney

[57] ABSTRACT

A new method is described for the preparation of a safe, immunogenic and efficacious vaccine for protection against the disease pertussis. In development of this vaccine, specific functional sites of pertussis toxin have been identified, and using this information, defined mutant holotoxins have been produced by site directed mutagenesis of the toxin gene. A number of these holotoxin analogues are detoxified, retain an immunodominant S1 epitope, are immunogenic and are protective in the standard pertussis vaccine potency test in mice.

8 Claims, 29 Drawing Sheets

OTHER PUBLICATIONS

J. Reiser et al.: "Expression in *Escherichia coli* of a *Bordetella pertussis* toxin-coding region" & Vaccines 86, New Approaches Immun. (Proc. Conf.) 1985 (Pub. 1986), 235–8.

Infection and Immunity, vol. 56, No. 8, Aug. 1988, pp. 1934–1941; J. T. Barbieri et al.: "ADP-ribosyl transferase mutations in the catalytic S-1 subunit of pertussis toxin".

Science, vol. 242, No. 4875, 1988, pp. 72-74.

Infection and Immunity, vol. 55, No. 4, Apr. 1987, pp. 963-967; A Nicosia et al.: "Expression and immunological properties of the five subunits of pertussis toxin".

Burnette et al; "Pertussis Toxin S1 Mutant with Reduced Enzyme Activity and a Conserved Protective Epitope".

Science-vol. 242, No. 487, 1988, pp. 72-74.

EP-A-0 145 486 (Glaxo Group Ltd.) p. 4, lines 12-27; p. 6, line 22, p. 9, line 12; example 2.

EP-A-0087 735 (Takeda Chemical Industries) p. 7, line 15-24.

Chemical Abstracts, vol. 106, No. 11, 16th Mar. 1987, p. 163, abstract No. 79657h, Columbus, Ohio, US.

J. M. Keith et al.: "Pertussis toxin gene cloning and expression of protective antigen", & US-A-843 727 (United States Dept. of Health and Human Services) Jun. 20, 1986 *Abstract*.

Chemical Abstracts, vol. 106, No. 5, 2nd Feb. 1987, p. 120, abstract No. 28346y, Columbus, Ohio US.

R. M. Brownlie et al.: "Complementation of mutations in *Escherichia coli* and *Bordetella pertussis* by B. pertussis DNA cloned in a broad-host-range cosmid vector", & J. Gen. Michrobiol. 1986, 132(11), 3221-9 *Abstract*.

FIG. 1.

AMINO ACID SEQUENCE OF RADIO LABELLED PEPTIDES

| CYCLE NO. | | | | | 5 | | | | | 10 | | | | 15 |
|---|---|---|---|---|---|---|---|---|---|---|---|---|---|---|
| PEPTIDE A | Ile | Leu | Ala | Gly | Ala | Leu | Ala | Thr | Tyr | Glu | Ser | * | Tyr | Leu | Ala |
| PEPTIDE B | Ile | Leu | - | Gly | Ala | Leu | Ala | Thr | Tyr | Glu | Ser | * | Tyr | Leu | Ala |
| | | | | | | | | | | | | | | |
| SUBUNIT S1 | Ile | Leu | Ala | Gly | Ala | Leu | Ala | Thr | Tyr | Glu | Ser | Glu | Tyr | Leu | Ala |
| RESIDUE NO. | | | | | 120 | | | | | 125 | | | | 130 |

\* UNCHARACTERIZED RADIOACTIVE AMINO ACID FOUND AT CYCLE 12

— NO AMINO ACID WAS IDENTIFIED AT THIS CYCLE

λgt II 15-4-1

λCh 35  Ch III

λCh 35  Ch121/Ch411

λCh 35   Ch 431

λCh 35   Ch 421

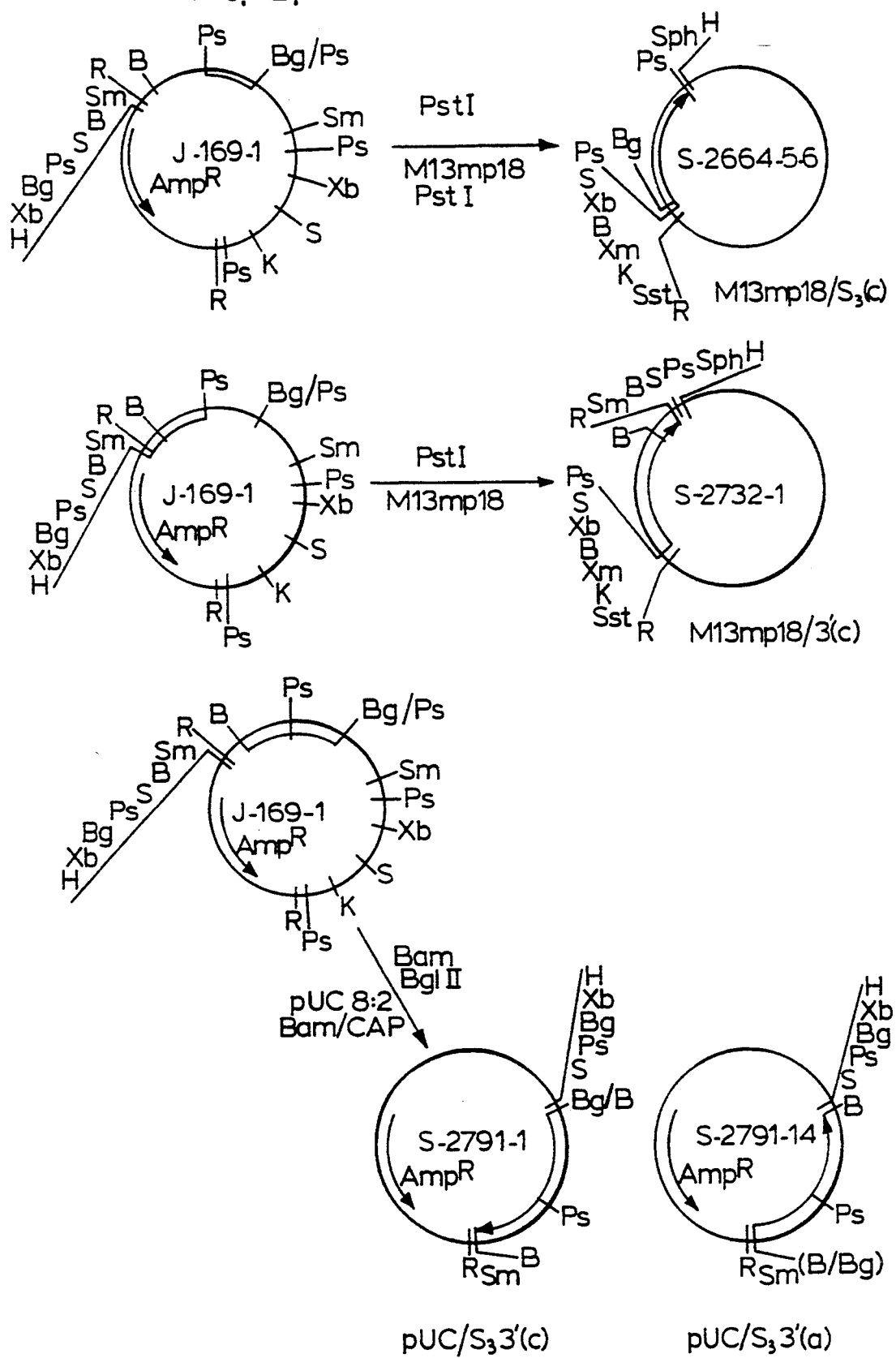

FIG 5.A.

```
GAATTCGTCGCCTCGGCCCTGGTTCGGCGTCATGGCCCCCAAGGAACCGACCCCAAGATAATCGTCCTGTCAACCGCCACATCAACGAGGCGCTGCAGTCCAAGGGCGTCG
TCGAGGCCCTTTGCCGCCCCAAGGCGCACGCGGTCATCGCCGGTTCATCGCAGACGAGATCCAGCGCTTGGGCGCGTCGTGTCGCGAACCGG
CGCCAAGCTGAAGTAGCAGCGCAGCCCTCCAACGCGCCATCCCGGTCCGGCCGATACGTTGGCAACGCCAACGGTGGCAGATTCGTCGTAC
AAACCCTCGATTCTTCCGTACATCCCGATCGAATGCAACACGGGCATGAACGCTCCTTCGGCGCAAAGTCGCCGATGGTACCGGTCACCGTCCGGACCGTGTGACCC
CCCTGCCATGGTGTCGTAAAATAGCCACCATCAAAACGCAGAGGGAAGACGGG    ATG CGT TGC ACT CGG GCA ATT CGC CAA ACC GCA AGA ACA
                                                        FMET ARG CYS THR ARG ALA ILE ARG GLN THR ALA ARG THR
                                                          1   2   3   4   5   6   7
                                                        S1
GGC TGG CTG ACG TGG CTG GCG ATT CTT GCC GTC ACG GCG CCC GCA GCG ACT TCG CCG GCA TGG GCC GAC GAT CCT CCC GCC ACC GTA
GLY TRP LEU THR TRP LEU ALA ILE LEU ALA VAL THR ALA PRO ALA TRP ALA ASP ASP PRO PRO ALA THR VAL
 8   9  10  11  12  13  14  15  16  17  18  19  20  21  22  23  24  25  26  27

TAC CGC TAT GAC TCC CGC CCG ATT CTT GCC GTC ACG GCG CCC GCA GCG ACT TCG CCG GCA TGG GCC GAC GAT CCT CCC GCC ACC GTA
TYR ARG TYR ASP SER ARG PRO GLU ASP VAL PHE GLN ASN GLY PHE THR ALA TRP GLY ASN ASN ASP ASN VAL LEU GLU HIS
  8   9  10  11  12  13  14  15  16  17  18  19  20  21  22  23  24  25  26  27  28  29  30  31  32  33  34  35

CTG ACC GGA CGT TCC TGC CAG GTC GGC AGC AAC AGC GCT TTC GTC TCC ACC AGC CGG CGC TAT ACC GAG GTC TAT
LEU THR GLY ARG SER CYS GLN VAL GLY SER SER ASN SER ALA PHE VAL SER THR SER ARG ARG TYR THR GLU VAL TYR
 36  37  38  39  40  41  42  43  44  45  46  47  48  49  50  51  52  53  54  55  56  57  58  59  60  61  62  63

CTC GAA CAT CGC ATG CAG AAT CGC GAG GTC GAG GCC CGC AGG GGC ACC GGC CAC TTC ATC GGC TAC ATC GAA GTC
LEU GLU HIS ARG MET GLN ASN ARG GLU VAL GLU ALA ARG ARG GLY THR GLY HIS PHE ILE GLY TYR ILE GLU VAL
 64  65  66  67  68  69  70  71  72  73  74  75  76  77  78  79  80  81  82  83  84  85  86  87  88  89  90  91

CGC GCC GAC AAC AAT TTC TAC GGC GCC GAA GTC GAG GCC CGC AGG GGC ACC GGC CAC TTC ATC GGC TAC ATC GAA GTC
ARG ALA ASP ASN ASN PHE TYR GLY ALA ALA SER SER TYR PHE GLU PHE VAL ASP THR TYR GLY ASP ASN ALA GLY ARG ILE LEU
 92  93  94  95  96  97  98  99 100 101 102 103 104 105 106 107 108 109 110 111 112 113 114 115 116 117 118 119
```

FIG.5.B.

```
GCC GGC GCG CTG GCC ACC TAC CAG AGC GAA TAT CTG GCA CAC CGG CGC ATT CCG CCC GAA AAC ATC CGC AGG GTA ACG CGG GTC
ALA GLY ALA LEU ALA THR TYR GLN SER GLU TYR LEU ALA HIS ARG ARG ILE PRO PRO GLU ASN ILE ARG ARG VAL THR ARG VAL
120 121 122 123 124 125 126 127 128 129 130 131 132 133 134 135 136 137 138 139 140 141 142 143 144 145 146 147

TAT CAC AAC ATC ACC GGC ACC ACG GAG ACG ACC AAC GCT CGC GAG CAG ACT CGC GCC AAT CCC
TYR HIS ASN ILE THR GLY THR THR GLU THR THR ASN ALA ARG GLU GLN THR ARG ALA ASN PRO
148 149 150 151 152 153 154 155 156 157 158 159 160 161 162 163 164 165 166 167 168 169 170 171 172 173 174 175

AAC CCC TAC ACA TCG GCA AGG TCC GTA GCG ATC GTC GGC ACA TTG CTG ACC ATG TGG GCG TGC ATG GCG
ASN PRO TYR THR SER ARG ARG ALA SER VAL GLY THR LEU VAL GLY MET ALA PRO VAL VAL GLY ALA CYS MET ALA
176 177 178 179 180 181 182 183 184 185 186 187 188 189 190 191 192 193 194 195 196 197 198 199 200 201 202 203

CGG CAG GCC GAA TCC GCA GCC ATG GCC GAG GCG ATG GTT CTC GTG TAC TAC AAG ACG CTC TGC CAT CTC TCC
ARG GLN ALA GLU SER ALA ALA MET ALA GLU ALA MET VAL LEU VAL TYR TYR LYS THR LEU CYS HIS LEU SER
204 205 206 207 208 209 210 211 212 213 214 215 216 217 218 219 220 221 222 223 224 225 226 227 228 229 230 231

GCG TAT TCG TTC TAGACCTGGCCAGCCCGCCCAACTCCGGTAATTGAACAGC ATG CCG ATC GAC CGC AAG ACG.CTC TGC CAT CTC TCC
ALA TYR SER PHE                                         fMET PRO ILE ASP ARG LYS THR LEU CYS HIS LEU LEU SER
232 233 234 235
                                                         S2

GTT CTG CCG TTG GCC CTC CTC GGA TCT CAC GTG GCG CGG GCC TCC ACG CCA GCC ATC GTC ATT CCG CAG GAA CAG ATT ACC
VAL LEU PRO LEU ALA LEU LEU GLY SER HIS VAL ALA ARG ALA SER THR PRO GLY ILE VAL ILE PRO PRO GLN GLU GLN ILE THR

CAG CAT GGC AGC CCC TAT GGA CGC TGC GCG GAA TTG CGC GAC GTG GCG GAA TTG CGC GGC GAT CTG CAG
GLN HIS GLY SER PRO TYR GLY ARG CYS ALA ASN LYS THR ARG ALA LEU THR VAL ALA GLU LEU ARG GLY ASP LEU GLN
```

FIG.5.C.

```
GAG TAC CTG CGT CAT GTG ACG CGC GGC TGG TCA ATA TTT GCG CTC TAC GAT GGC ACC TAT CTC GGC GAA TAT GGC GGC GTG
GLU TYR LEU ARG HIS VAL THR ARG GLY TRP SER ILE PHE ALA LEU TYR ASP GLY THR TYR LEU GLY GLU TYR GLY GLY VAL

ATC AAG GAC GGA ACA CCC GGC GGC GCA TTC GAC CTG AAA ACG ACG TTC TGC ATC ATG ACC ACG CGC AAT ACG GGT CAA CCC GCA
ILE LYS ASP GLY THR PRO GLY GLY ALA PHE ASP LEU LYS THR THR PHE CYS ILE MET THR THR ARG ASN THR GLY GLN PRO ALA

ACG GAT CAC TAC TAC AGC GTC ACC GCC ACT CGC CTC TCC AGC ACC AAC AGC AGG CTA TGC GCG GTC TTC GTC AGA AGC
THR ASP HIS TYR TYR SER ASN VAL THR ALA THR ARG LEU SER SER THR ASN SER ARG LEU CYS ALA VAL PHE VAL ARG SER

GGG CAA CCG GTC ATT GGC GCC TGC ACC AGC CCG TAT GAC GGC AAG TAC AGC ATG TAC AGC CGG CTG CGG AAA ATG CTT TAC
GLY GLN PRO VAL ILE GLY ALA CYS THR SER PRO TYR ASP GLY LYS TYR SER MET TYR SER ARG LEU ARG LYS MET LEU TYR

CTG ATC TAC GTG GCC GGC ATC TCC GTA CGC GTC CAT GTC AGC AAG GAA GAA CAG TAT TAC GAC TAT GAG GAC GCA ACG TTC GAG
LEU ILE TYR VAL ALA GLY ILE SER VAL ARG VAL HIS VAL SER LYS GLU GLU GLN TYR TYR ASP TYR GLU ASP ALA THR PHE GLU

ACT TAC GCC CTT ACC GGC ATC TCC ATC TGC AAT CCT GGA TCA TCC TTA TGC TGAGACGCTTCCCCACTGAACCACCGCCCCCGGACAGGGCGG
THR TYR ALA LEU THR GLY ILE SER ILE CYS ASN PRO GLY SER SER LEU CYS

CGCCCGGCGGTCGCGC GTG CGC GCC CTG CGC TTG CTG GCA TCC GCG ATG CAT CTT TCC CCC GCC CTG GCC GAC GTT CCT
                 VAL ARG ALA LEU ARG LEU LEU ALA SER ALA MET HIS LEU SER PRO ALA LEU ALA ASP VAL PRO
                 fMET ARG ALA LEU ALA TRP LEU LEU ALA SER GLY ALA MET THR HIS LEU SER PRO ALA LEU ALA ASP VAL PRO
                      24
```

FIG.5D.

```
TAT GTG CTG AAG ACC AAT ATG GTG ACC AGC GTA GCC ATG AAG CCG TAT GAA GTC ACC CCG ACG CGC ATG CTG GTC TGC
TYR VAL LEU LYS THR ASN MET VAL VAL THR SER VAL ALA MET LYS PRO TYR GLU VAL THR PRO THR ARG MET LEU VAL CYS

GGC ATC GCC GCC AAA CTG GGC GCC GCC AGC CCG GAC GCG CAC GTG CCG TTC TGC TTC GGC AAG GAT CTC AAG CGT CCC
GLY ILE ALA ALA LYS LEU GLY ALA ALA SER PRO ASP ALA HIS VAL PRO PHE CYS PHE GLY LYS ASP LEU LYS ARG PRO

GGC AGC AGT CCC ATG GAA GTC ATG TTG CGC GCC GTG TTC ATG CAA CGG CCG CTG CGC ATG TTT CTG GGT CCC AAG CAA CTC
GLY SER SER PRO MET GLU VAL MET LEU ARG ALA VAL PHE MET GLN ARG PRO LEU ARG MET PHE LEU GLY PRO LYS GLN LEU

ACT TTC GAA GGC AAG CCC GCG CTC ATC CGG CTG ATG GTC GAA TGC AGC GGC AAG CAG GAT TGC CCC TGA AGCCGACCCC ATG
THR PHE GLU GLY LYS PRO ALA LEU ILE ARG LEU MET VAL GLU CYS SER GLY LYS GLN ASP CYS PRO                fMET
                                                                                                        S5

CAT ACC ATC GCA TCC ATC CTG TTG TCC GTG CTC GGC ATA TAC AGC CCG GCT GAC GTC GCC GGC TTG CCG ACC CAT CTG TAC AAG
HIS THR ILE ALA SER ILE LEU LEU SER VAL LEU GLY ILE TYR SER PRO ALA ASP VAL ALA GLY LEU PRO THR HIS LEU TYR LYS

AAC TTC ACT GTC CAG GAG CTG GCC TTG AAG AAT CAG GAG TTC TGC CTG ACC GCC TTC ATG TCG GGC AGA AGC
ASN PHE THR VAL GLN GLU LEU ALA LEU LYS ASN GLN GLU PHE CYS LEU THR ALA PHE MET SER GLY ARG SER

CTG GTC CGG GCC GCA TGC CTG TCC GAC GAG CAC GAC ACG TGG TTC GAC CAC CAT CTT GCC ATA TCC GCG TAT
LEU AVL ARG ALA ALA CYS LEU SER ASP ASP ALA GLY HIS GLU HIS ASP THR MET LEU GLY PHE ALA ILE SER ALA TYR

GCG CTC AAG AGC CGG ATC GCG GTG GAA GAC TCG CCG TAT CCG GGC GAT CTG CTC GAA CTG CTC ATC TGC
ALA LEU LYS SER ARG ILE ALA LEU THR VAL GLU ASP SER PRO TYR PRO GLY ASP LEU LEU GLU LEU LEU GLN ILE CYS
```

FIG. 5E.

CCG CTC AAC GGA TAT TGC GAATGAACCCTTCCGGAGGTTTCGACGTTTCCGCGCAATCCGCTTGAGACGATCTTCCGCCCTGGTTCCATTCCGGGAACACCGCAAC
PRO LEU ASN GLY TYR CYS GLU

ATG CTG ATC AAC AAC AAG AAG CTT CAT CAC ATT CTG CCC ATC CTG GTG CTC GCC CTG GTC CTG GGC ATG CGC ACG GCC CAG GCC
fMET LEU ILE ASN LYS LYS LEU HIS HIS ILE LEU PRO ILE LEU VAL LEU ALA LEU VAL LEU GLY MET ARG THR ALA GLN ALA
$3

GTT GCG CCA GGC ATC GTC ATC CCG AAG GCA CTG TTC ACC CAA CAG GGC GGC TAT GGA CGC CCG AAC GGA ACC CGC
VAL ALA PRO GLY ILE VAL ILE PRO LYS ALA LEU PHE THR GLN GLN GLY GLY TYR GLY ARG PRO ASN GLY THR ARG
 1   2   3   4   5   6   7   8   9  10  11  12  13  14  15  16  17  18  19  20  21  22  23  24  25  26  27  28

GCC TTG ACC GTG GCC GAA CTG CGC AAC GGC GAA TTG CAG ACG TAT TTG CGC CAG ATA ACG CCC GGC TGG TCC ATA TAC GGT
ALA LEU THR VAL ALA GLU LEU ARG ASN GLY GLU LEU GLN THR TYR LEU ARG GLN ILE THR PRO GLY TRP SER ILE TYR GLY
 29  30  31  32  33  34  35  36  37  38  39  40  41  42  43  44  45  46  47  48  49  50  51  52  53  54  55  56

CTC TAT GAC GGT ACG CTG GGC CAG GCA TAC GGC ATC ATC AAG GAC GCA CCG GGC GCA GGG TTC ATT TAT CGC GAA
LEU TYR ASP GLY THR LEU GLY GLN ALA TYR GLY ILE ILE LYS ASP ALA PRO GLY ALA PHE ILE TYR ARG GLU
 57  58  59  60  61  62  63  64  65  66  67  68  69  70  71  72  73  74  75  76  77  78  79  80  81  82  83  84

ACT TTC TGC ATC ACG ACC ATA TAC AAG ACC GGG CAA CCG GCT GCG GAT CAC GAT CAC AAG GTC ACG CGC CTG CTC
THR PHE CYS ILE THR THR ILE TYR LYS THR GLY GLN PRO ALA ALA ASP HIS TYR SER VAL THR ALA THR ARG LEU LEU
 85  86  87  88  89  90  91  92  93  94  95  96  97  98  99 100 101 102 103 104 105 106 107 108 109 110 111 112

FIG. 5F.

```
GCC AGC ACC AAC AGC AGG CTG TGC GCG GTA TTC GTC AGG GAC GGG CAA TCG GTC ATC GGA GCC TGC GCC AGC CCG TAT GAA GGC
ALA SER THR ASN SER ARG LEU CYS ALA VAL PHE VAL ARG ASP GLY GLN SER VAL ILE GLY ALA CYS ALA SER PRO TYR GLU GLY
113 114 115 116 117 118 119 120 121 122 123 124 125 126 127 128 129 130 131 132 133 134 135 136 137 138 139 140

AGG TAC AGA GAC ATG TAC GAC GCG GCG CTG CTG CGC CGG CTG CTG TAC ATG ATC TAT ATG TCC GTA CGC GTC CAC GTC AGC
ARG TYR ARG ASP MET TYR ASP ALA ALA LEU LEU ARG ARG LEU LEU TYR MET ILE TYR MET SER VAL ARG VAL HIS VAL SER
141 142 143 144 145 146 147 148 149 150 151 152 153 154 155 156 157 158 159 160 161 162 163 164 165 166 167 168

AAG GAA GAG CAG TAT TAC GAC TAC GAG GAC GCC ACA TTC CAG ACC TAT GCC CTC TGC AAC CCG GCA GCG
LYS GLU GLU GLN TYR TYR ASP TYR GLU ASP ALA THR PHE GLN THR TYR ALA LEU CYS ASN PRO ALA ALA
169 170 171 172 173 174 175 176 177 178 179 180 181 182 183 184 185 186 187 188 189 190 191 192 193 194 195 196

TCG ATA TGC TGAGCCGCCCGGCTGCACCCGTTGTTCGCTGTCCATGTTTTCCTTGACGGATAACCGCGAATGAATGAAAGACTTGAGAGCATCGCTACCGCCCT
SER ILE CYS
197 198 199

GGCCTTCATGGCAGCCTGCACCCGTTGTTCGCTGTCCATGTTTTCCTTGACGGATAACCGCGAATGAATCCCTTGCCGCCCGGCCGGGCTGCAGGCCGCTGAAGCCGGCATCATGGCAGCCGTCAACCACTTCATGGCGAGCATCGTGGTCGTACTGC
CCGGCGCGCTCAGTGCCCACGGTGACCATGCCATATAATCTGGGGCGGGCCTACAAGCTGCTGTTCCGGCGGCCGATGCTGCTTCCGGAGTGGTCCTGGCCGGGACTGC
TGATCGGCGCATCGGCCGAAATCGCTGCCCGTTATCGTCGTTATCGACGTATCAACATGCTGATCCTCTTTCAAGGGCTGCACCCGGCCGATGCTGATGGG
CGTACCGCCGCCGATGACCAGCAGTTCCGCCTGATC
ATGATCGGCGCGATGACCAGCAGTTCCGCCCTGATC
```

*DENOTES THE LOCATION OF MUTATIONS IN THE S₁ GENE

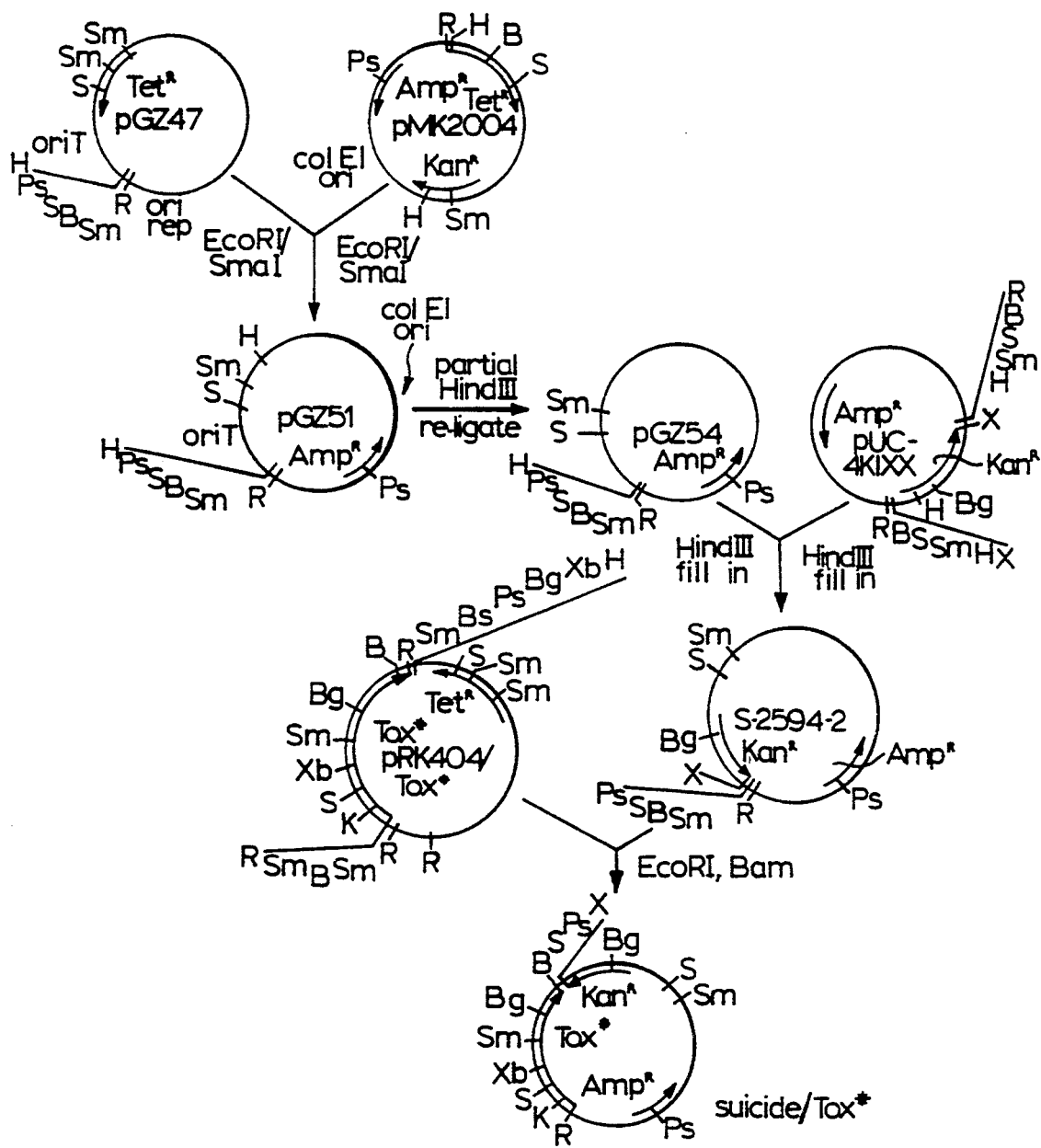

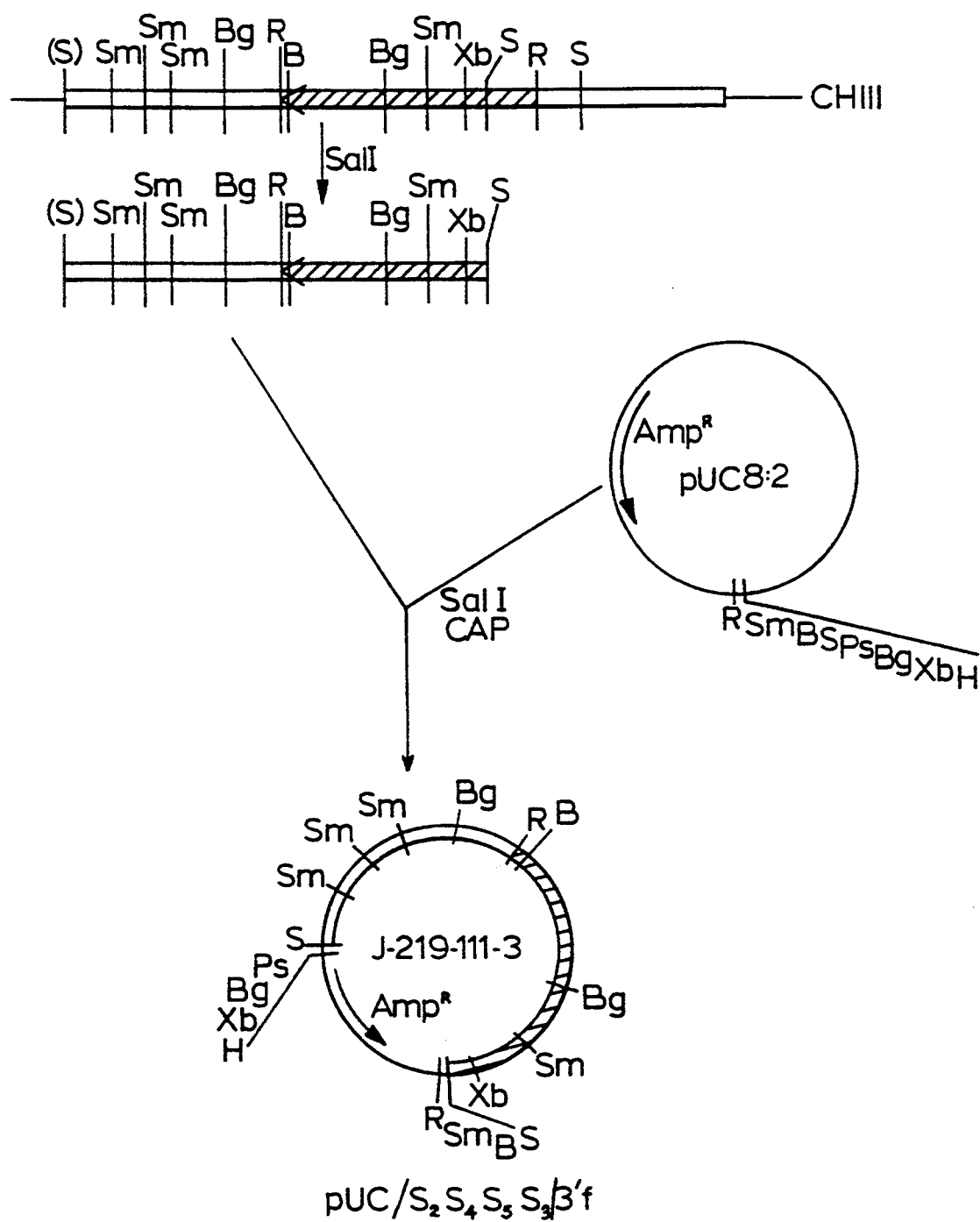

Deletion of the endogenous TOX operon from B. pertussis and the integration of mutated TOX alleles Southern blot analysis of a recombinant B. pertussis strain

FIG. 13

Kinetics of antigen production by recombinant B. pertussis strain 989-56 (Lys9 Gly129) in 10L

REVERSE-PHASE HPLC AND SDS-PAGE OF WILD-TYPE PT AND GLY 129 MUTANT

GENETIC DETOXIFICATION OF PERTUSSIS TOXIN

REFERENCE TO RELATED APPLICATION

This is a division of application Ser. No. 589,423, filed Sep. 28, 1990, now U.S. Pat. No. 5,244,657, which is a continuation-in-part of copending U.S. patent application Ser. No. 275,376 filed Nov. 23, 1988, now U.S. Pat. No. 5,085,862.

FIELD OF INVENTION

The present invention relates to a novel method for the detoxification of pertussis toxin by the genetic manipulation of DNA segments coding for one or more amino acid residues essential for the toxin's biological activity. It also relates to a procedure for the creation of genetically altered *Bordetella pertussis* bacteria that produce the detoxified pertussis toxin.

BACKGROUND OF THE INVENTION

Whooping cough, or pertussis, is a severe, highly contagious respiratory disease of infants and young children caused by infection with *Bordetella pertussis*. Owing to the many virulence factors associated with this organism, the pathogenesis of the disease is still not fully understood; however, it is generally recognized that the major systemic effects are caused by pertussis toxin (PT). This material exhibits a wide range of biological activities as illustrated by such alternative names as lymphocytosis-promoting factor, histamine-sensitizing factor and islet-activating protein. Many of these effects are associated with its biochemical function as an adenosine diphosphate (ADP)-ribosyltransferase. ADP-ribosylation of certain acceptor guanosine triphosphate-binding proteins leads to a loss of control over a variety of metabolic pathways mediated by cyclic adenosine monophosphate and by phospholipase C. In the absence of a protein acceptor, PT also catalyses the hydrolysis of nicotinamide adenine dinucleotide (NAD glycohydrolase activity).

Conventional killed whole-cell pertussis vaccines contain a mixture of antigens and there has been a great deal of work towards the development of a defined acellular vaccine comprising specific protective antigens. PT is the most significant protective antigen. Other antigens under consideration are agglutinogens, filamentous hemagglutinin (FHA) and the 69 KD outer membrane protein.

Normally PT and other antigens are chemically inactivated, or toxoided, using agents such as formaldehyde, glutaraldehyde or hydrogen peroxide. This approach has the serious disadvantage that a delicate balance must be sought between too much and too little chemical modification. If the treatment is insufficient, the vaccine may retain residual toxicity owing to the presence of a small proportion of unchanged virulence factors including PT. If the treatment is too excessive, the vaccine may lose potency because its native immunogenic determinants are masked or destroyed. This problem is of particular concern in the case of PT, since the catalytic subunit is comparatively difficult to inactivate by aldehydes. The possible residual toxicity or reversion of toxoided whole-cell pertussis vaccines has been questioned for many years, and it has been suggested that in rare cases the vaccine might cause major neurological damage. All pertussis vaccines that are in use at present, or in the trial stages, depend on the inactivation of the antigens by chemical means, which introduces the problems previously mentioned. It is obvious that if an inactivated vaccine could be designed without resorting to the toxoiding process, but preserving the native structure of immunogenic and protective epitopes, an additional degree of safety and efficacy would be added. For these reasons the inventors have genetically manipulated the gene coding for PT (TOX), and constructed strains of *B pertussis* that secrete non-toxic PT analogues.

In its structural organization, PT belongs to the family of ADP-ribosyltransferase bacterial toxins, which also includes diphtheria toxin, *Pseudomonas aeruginosa* exotoxin A, cholera toxin and *Escherichia coli* heat labile toxin. Accordingly, it consists of two functional moieties; namely an A portion, which carries the enzymic activity, and a B portion, which binds to the host cell and permits translocation of the A portion to its site of action. In PT, the A portion is a discrete subunit, commonly denoted S1. The B portion is a non-covalent oligomer of five polypeptides arranged as two dimers, comprising subunits S2 plus S4 and subunits S3 plus S4 respectively, held together by a joining subunit S5.

The amino acid sequence of the S1 subunit reveals several features of interest. There are only two cysteine residues which form an intrachain disulphide bond; however, it is known that for enzymic activity the toxin must be reduced (Moss et al., J. Biol. Chem. 258, 11872, [1983]), indicating the importance of these residues. There are two tryptophans in S1, and it has been suggested that tryptophan residues are close to the NAD binding sites of diphtheria toxin and *P. aeruginosa* exotoxin A. Two conserved regions in S1 are also found in the amino acid sequences of cholera toxin and *E. coli* heat labile toxin (Locht & Keith, Science, 232, 1258, [1986]). In addition the NAD active sites of diphtheria toxin and *P. aeruginosa* exotoxin A have been shown to contain a glutamic acid residue (Carrol & Collier, Proc. Nat. Acad. Sci., U.S.A., 81, 3307, [1984]; Carroll & Collier, J. Biol. Chem., 262, 8707, [1987]).

As noted above, the B portion of PT mediates its binding to cellular receptors and contains two dimers. Whether each of these dimers bears a binding site remains controversial. However, the S2 and S3 subunits are similar in amino acid sequence and binding studies have indicated that lysine and/or tyrosine residues of S3 in particular are implicated in the interaction of the toxin with its receptor. (Nogimori et al., Biochem., 25, 1355, [1986]; Armstrong & Peppler, Infect. Immun., 55, 1294, [1987]).

Site-directed mutagenesis of diphtheria toxin and *P. aeruginosa* exotoxin A at the NAD-interacting glutamic acid residues has led to significant reduction in ADP-ribosyltransferase activity (Tweten et al., J. Biol. Chem., 260, 10392, [1984]; Douglas & Collier, J. Bacteriol., 169, 4967, [1987]). Complete truncated forms of S1 and S2 have been expressed in *E. coli* (Locht et al., Infect. Immun., 55, 2546, [1987]). Mutations of the TOX operon generated by transposon insertion, gene truncation or linker insertion have been introduced by allelic exchange into the chromosome of *B. pertussis* (Black et al., Ann. Sclavo, 175, [1986], European Patent Publication No. 275,689; Black & Falkow, Infect. Immun., 55, 2465, [1987]). However, the biological and immunoprotective properties of fully-assembled recombinant holotoxins specifically detoxified by site-directed mutagenesis of functional amino acid residues have not been reported. The generation of such PT analogues for inclusion in a safe and efficacious pertussis vaccine is the subject of this invention.

The applicants are further aware of European Patent Publication 306,318 ("Amgen") and European Patent Publication 322,533 ("Sclavo"). Both publications disclose mutagenic alteration of the S1 subunit of pertussis toxin in an attempt to provide a non-toxic vaccine and recognize that the S1 subunit carries an important immunogenic epitope. Both publications also disclose combining the mutated S1 subunit with other subunits to obtain optimum immunogenicity. However, neither publication provides evidence of immunoprotective properties against pertussis and, indeed, the S1 subunit itself is not immunoprotective In addition, neither reference produces a mutant holotoxin in a B. pertussis host, or other Bordetella organism, as in the present invention. Both publications express subunits from E. coli and similar organisms. It is not possible to produce the mutant holotoxin from E. coli.

In one aspect of the invention, mutagenesis of residues in both the A and B proteins of the pertussis toxin is carried, to provide immunoprotective holotoxins. Both references are silent with respect to such a possibility.

In testing for the efficacy and toxicity of materials that could be candidates for a protective vaccine, there are a number of in vivo and in vitro assays available. The standard test for potency is the mouse protection test, which involves intra-cerebral challenge with live B. pertussis. Newer vaccine tests measure the production of protective antibodies. A common toxicity test is the CHO (Chinese hamster ovary) cell clustering assay, which reflects both the ADP-ribosyltransferase and binding ability of the toxin (Burn et al., Infect. Immun., 55, 24, [1987]). A direct test of the enzymic activity of PT is the ADP-ribosylation of bovine transducin (Walkins et al., J. Biol. Chem., 260, 13478, [1985]).

SUMMARY OF INVENTION

In accordance with the present invention, there is provided a novel method of detoxifying PT, which does not suffer from the drawbacks of the prior art chemical methods and yet provides detoxified PT that retains its immunological properties without possessing undesirable side effects. In the present invention, amino acid residues of the toxin that are crucially important to its functional and toxic activities are identified. These residues are subsequently removed or replaced by site-directed mutagenesis of the isolated toxin gene. The mutated toxin operon resulting from such manipulations then is substituted for the native gene in the organism, which thereby produces the non-toxic analog of the toxin under normal growth conditions. In this manner, the three-dimensional structure and thus the immunogenicity of the PT analogue is minimally impaired. Indeed, an appropriate mutant form of the toxin on its own may provide satisfactory protection against the severe symptoms of pertussis, though other components may be required to establish resistance against the bacterial infection itself.

In accordance with one aspect of the present invention, therefore, there is provided an immunoprotective genetically-detoxified mutant of pertussis holotoxin. By the term "genetically-detoxified" as used herein is meant a pertussis holotoxin mutant which exhibits a residual toxicity of about 1% or less, preferably less than about 0.5%, of that of the native toxin. The residual toxicity is determined by CHO cell clustering assay and ADP-ribosyltransferase activity.

In accordance with another aspect of the present invention, there is provided a vaccine against Bordetella pertussis comprising an immunogenically-effective amount of the immunoprotective mutant of pertussis holotoxin or a toxoid thereof and a physiologically-acceptable carrier therefor. The genetically-detoxified pertussis holotoxin also may be used as a carrier protein for hapten, polysaccharides or peptides to make a conjugate vaccine against antigenic determinants unrelated to the holotoxin.

A further aspect of the present invention provides a method of production of the mutant, which comprises identifying at least one amino acid residue of the holotoxin which confers toxicity to the toxin; effecting site-directed mutagenesis of the holotoxin gene to remove or replace at least one such residue and to produce a mutated holotoxin operon; substituting the mutated holotoxin operon for the native gene in a Bordetella organism; and growing the transformed organism to produce an immunoprotective, genetically-detoxified holotoxin.

As will be apparent from the following disclosure, the present invention further provides novel strains of Bordetella pertussis from which the toxin operon has been removed or has been replaced by a mutant gene as provided herein.

BRIEF DESCRIPTION OF DRAWINGS

FIG. 1 shows the sequences of amino acids obtained by automated sequencing of radiolabelled peptides A and B from subunit S1 which are compared with residues from mature S1;

FIGS. 4A–4E show the construction of subclones of the TOX gene used for sequencing the operon. In FIG. 4A, a restriction map of the TOX gene and the protein subunits are indicated, with clones being derived from the pUC8:2/TOX clone J-169-1, and the subunit genes being subcloned into M13mp18, M13mp19 or pUC8:2, as indicated; in FIG. 4B, clones of the 5' region of pUC8:2, S1 in M13mp18 and S1 in M13mp19 clones are described; in FIG. 4C, clones of S2 in M13mp18 and M13mp19 are shown; in FIG. 4D, clones of S4/S5 in M13mp18 and M13mp19 are shown; and, in FIG. 4E, clones of S3 and the 3' region in M13mp18 and pUC8:2;

FIGS. 5A, 5B, 5C, 5D, 5E and 5F shows the nucleotide sequence and structural gene translation products of the B. pertussis 10536 TOX gene;

In FIGS. 6A and FIG. 6B, there is shown the construction of primary TOX analogue genes in pRK404 from mutated genes and native genes, in FIG. 6C, there is shown a typical construction of a "crossed" mutant from two S1-mutated genes, and in FIG. 6D, there is shown the construction of replicating plasmids containing mutations of the S2 sub-unit;

FIG. 7 shows the development of a "suicide" plasmid, one capable of conjugative transfer but not replication, based on pRK404 and pMK2004 (Kahn et al., Methods in Enzymology, 68, 278, [1979]), for non-homologous recombination. The final plasmids also contain a kanamycin resistance gene 3' of the TOX or TOX analogue genes;

FIGS. 8A–8C show the cloning of the 5'- and 3'-flanking region of the TOX gene. FIG. 8A shows the construction of the 5'-portion of TOX in pUC8:2 from the λ Charon 35 clone Ch421; FIG. 8B shows the construction of the 3'-portion of TOX in pUC8:2 from λ Ch 111; and FIG. 8C shows the generation of a pUC8:2 clone containing TOX plus its 5'- and 3'-flanking regions;

FIG. 13 shows a Southern blot analysis of the reintegration of a TOX allele into the chromosome of B, pertussis;

GENERAL DESCRIPTION OF INVENTION

Figure 2:
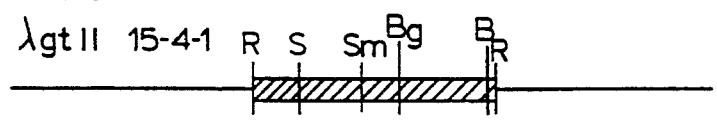
FIGS. 2–2E show the structures of various TOX clones obtained from the chromosomal libraries.
Figure 2B:
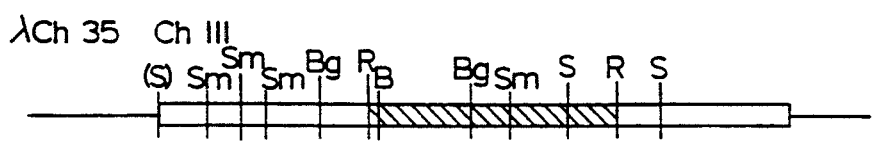
Figure 2C:
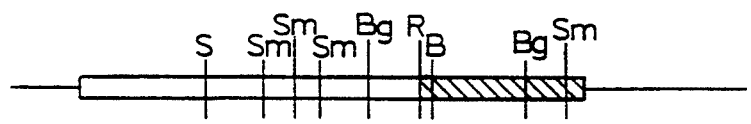
Figure 2D:
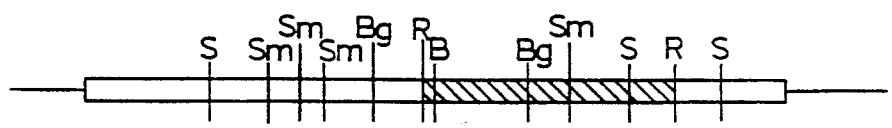
Figure 2E:
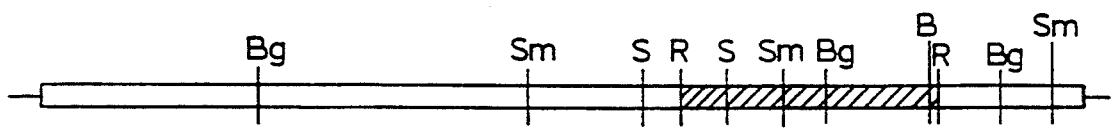
Figure 3:
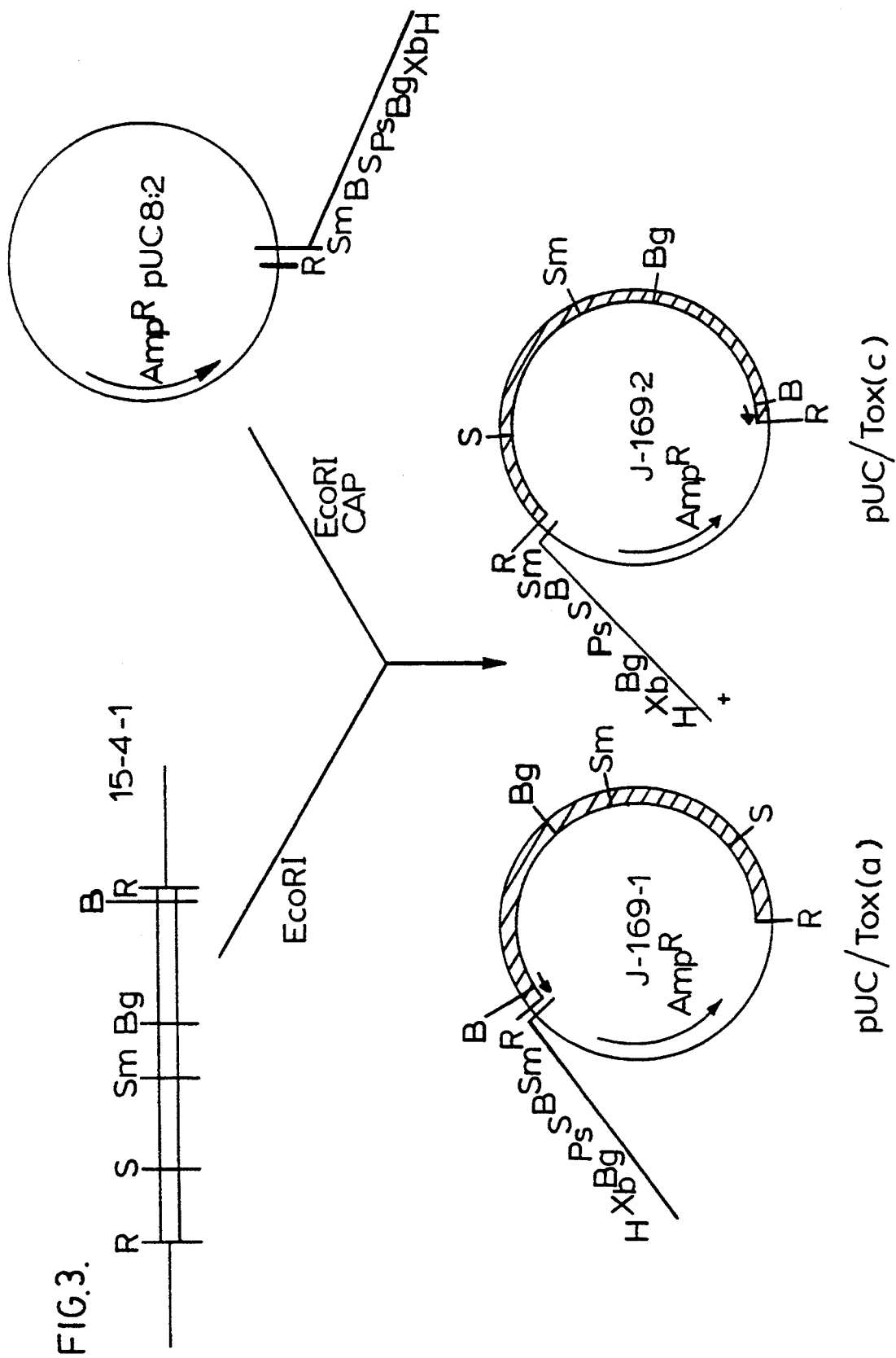
FIG. 3 shows the construction of subclones containing the TOX gene from the genomic clone λ gtII 15-4-1, with the TOX gene being inserted into the multiple cloning site of pUC8:2, which contains Bgl II and Xba I sites.
Figure 4A:
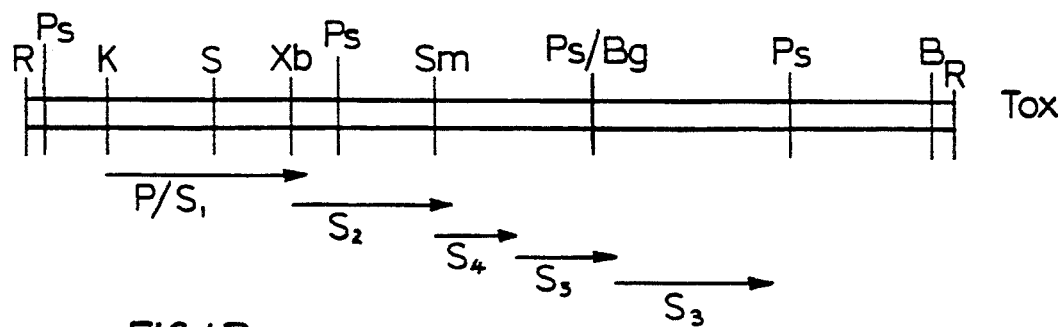
Figure 4B:
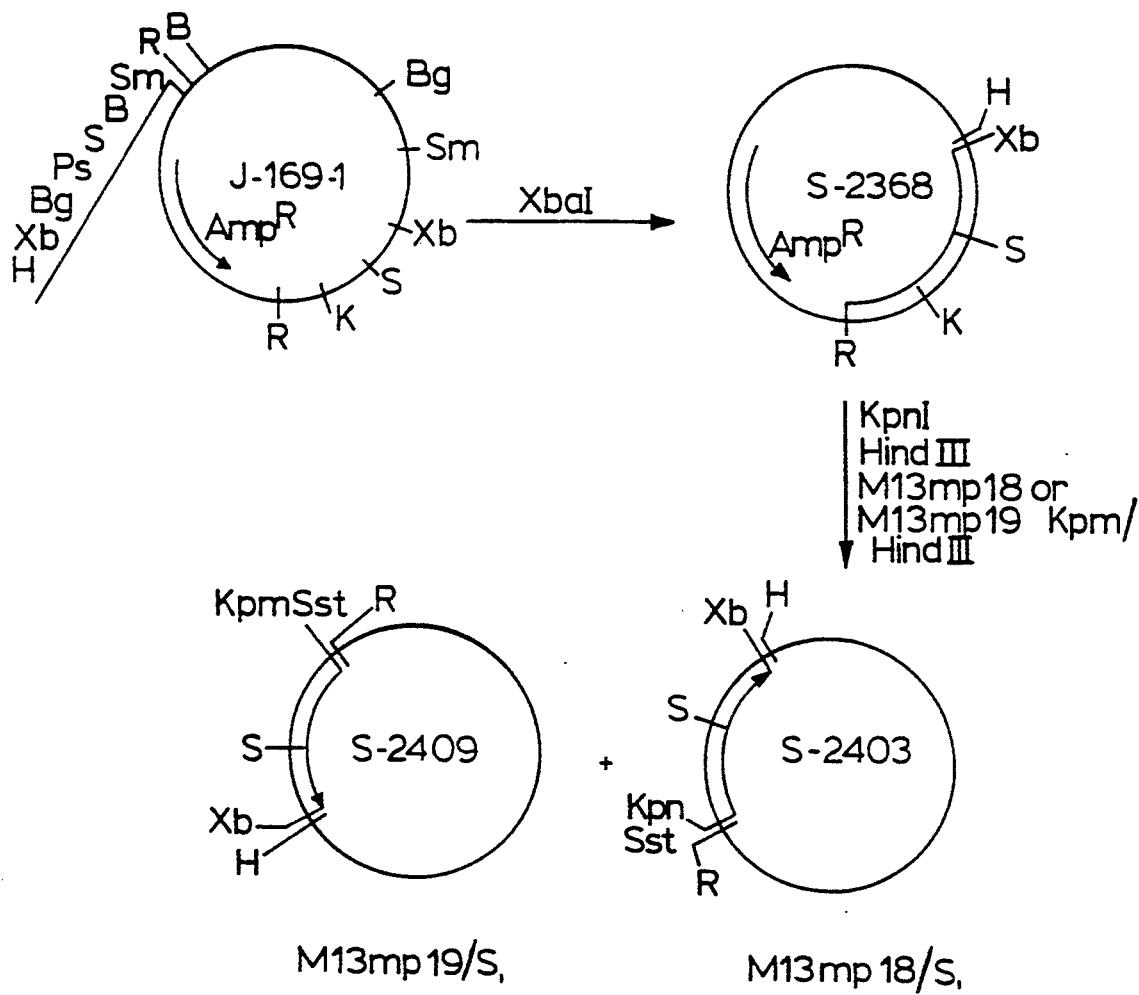
Figure 4C:
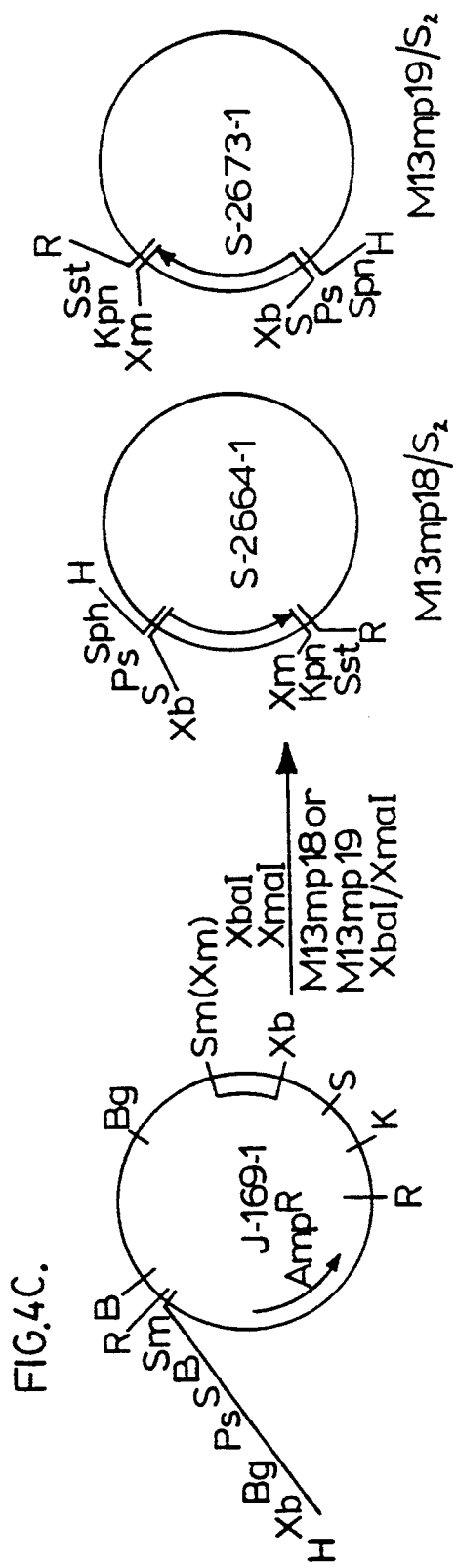
Figure 4D:
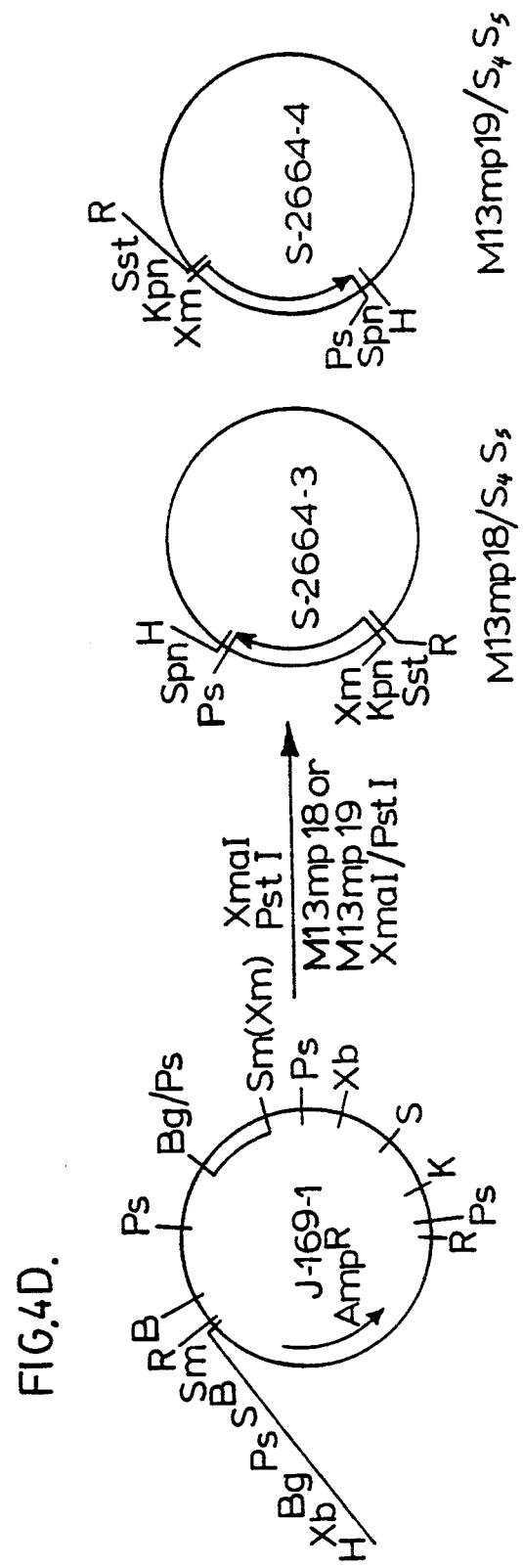
Figure 6A:
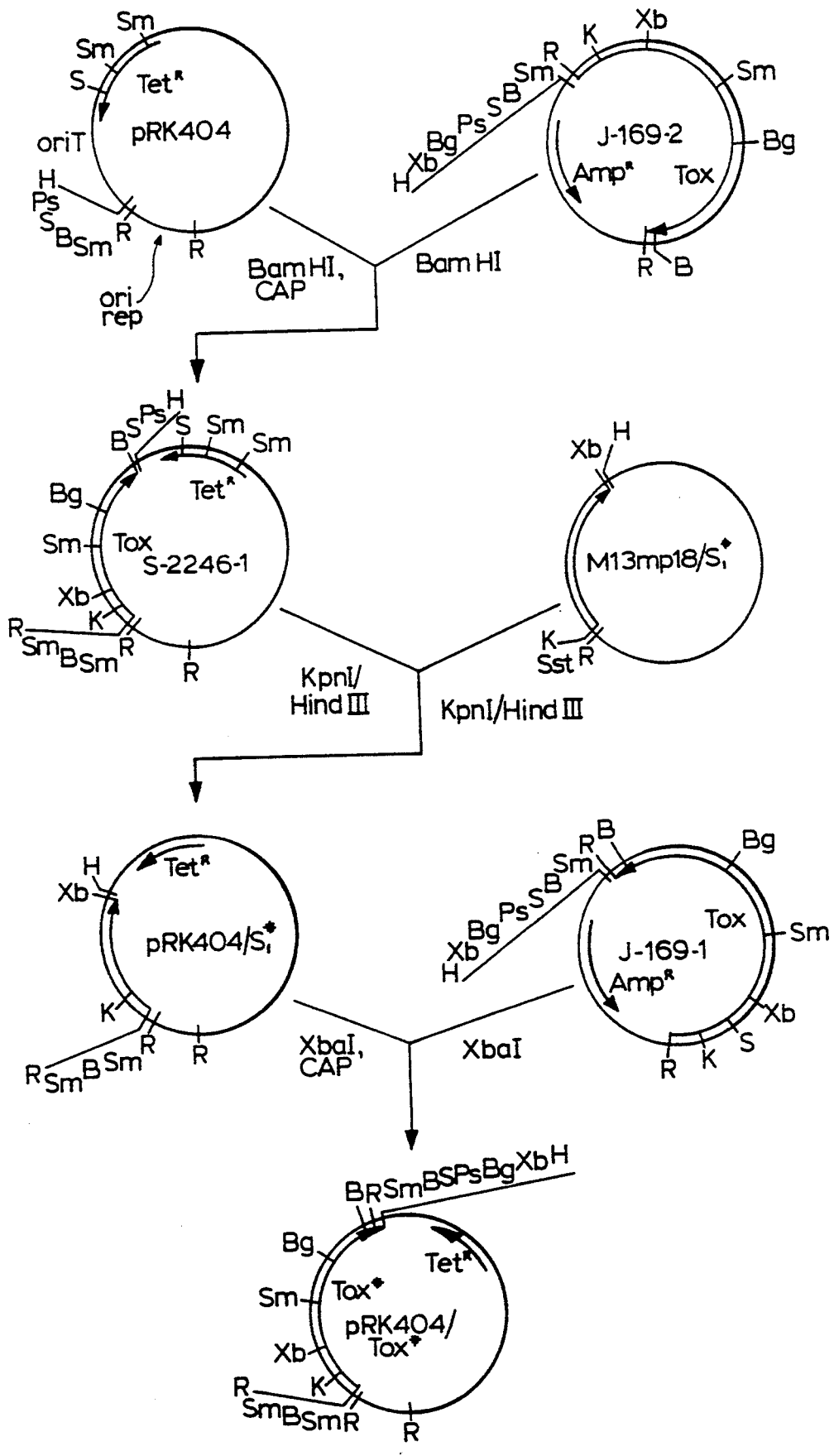
FIGS. 6A–6D show the construction of TOX or TOX analogue genes in the broad-host-range plasmid pRK404 (Ditta et al., Plasmid, 13, 149, [1985]).
Figure 6B:
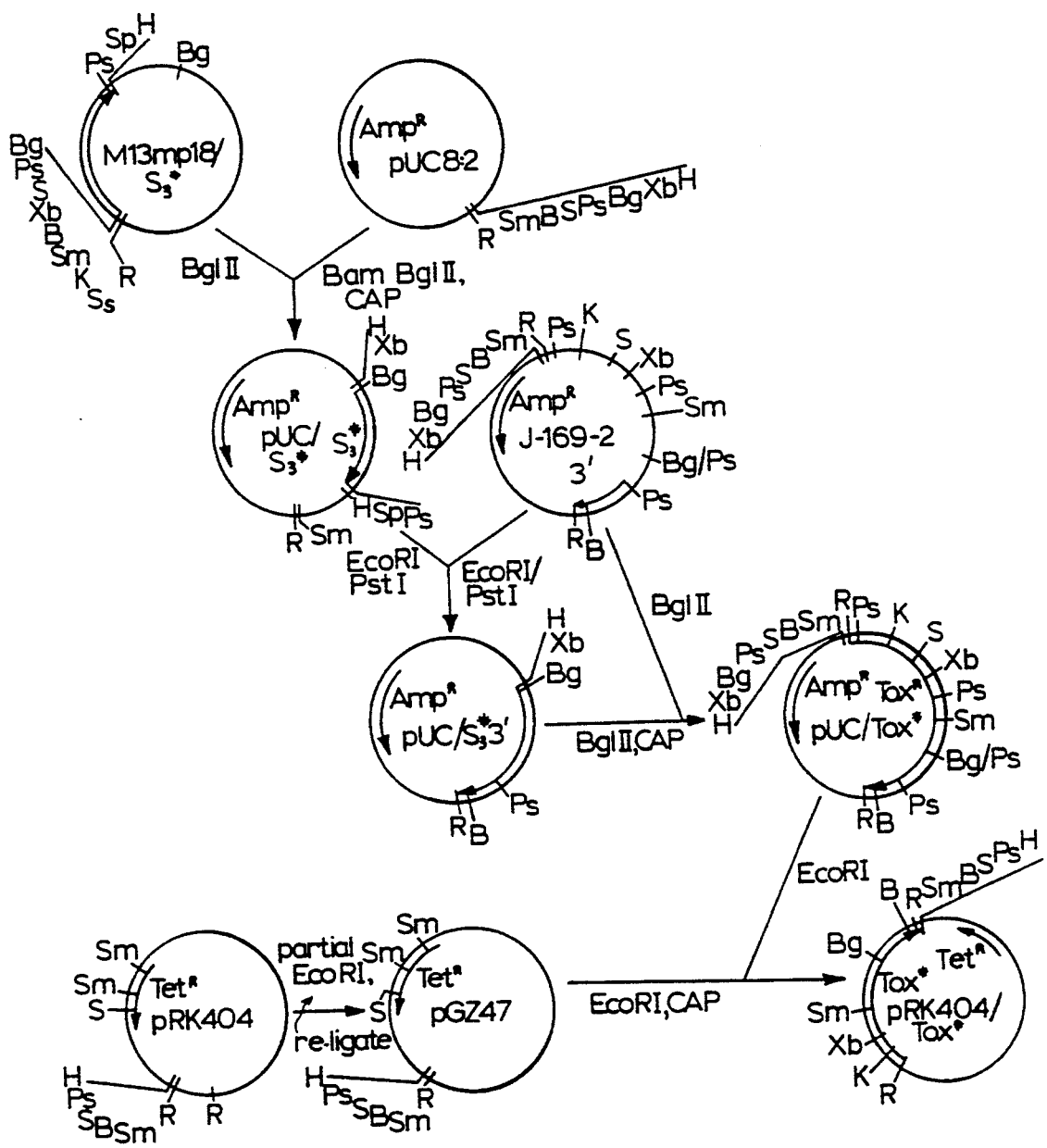
Figure 6C:
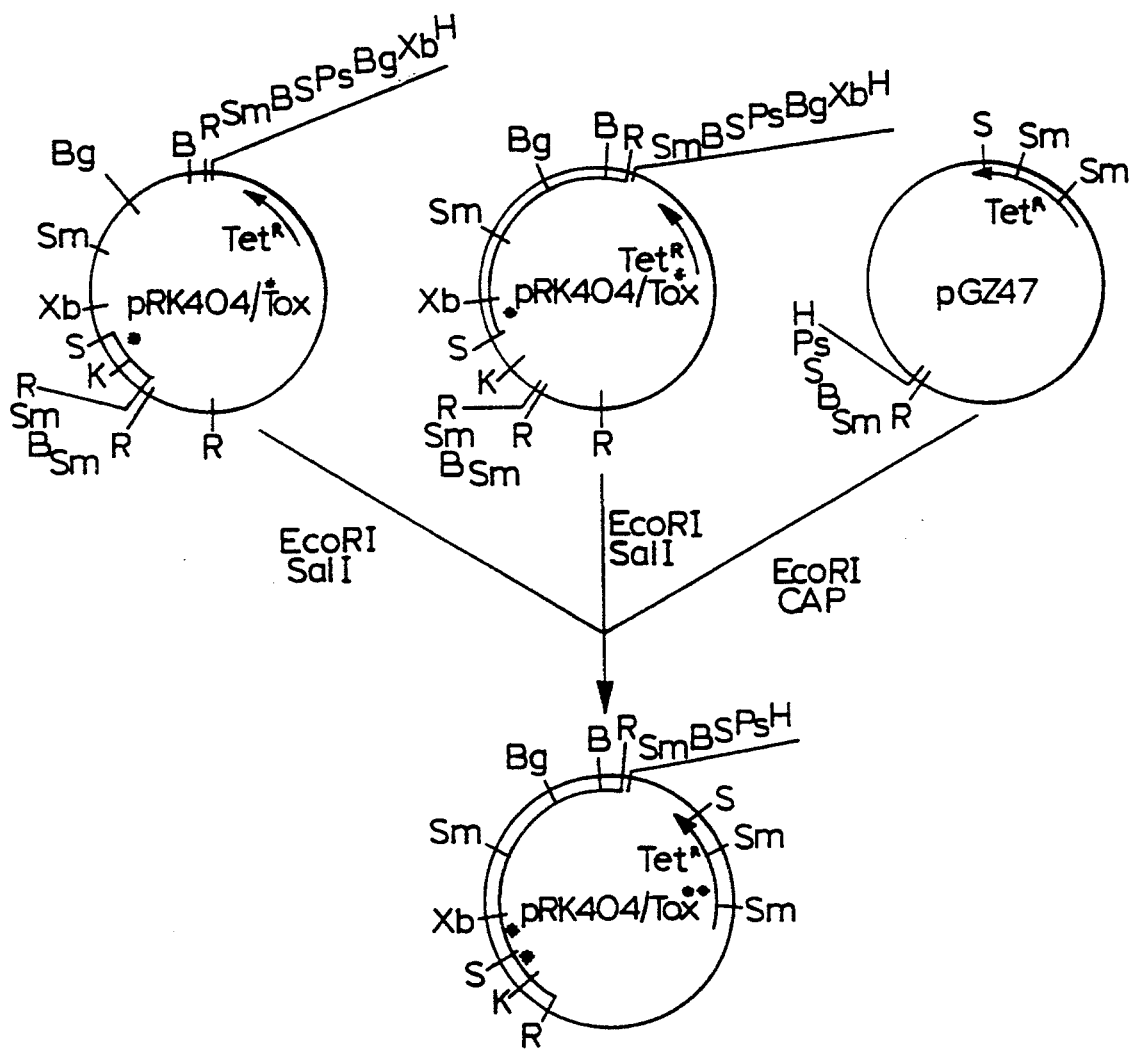
Figure 6D:
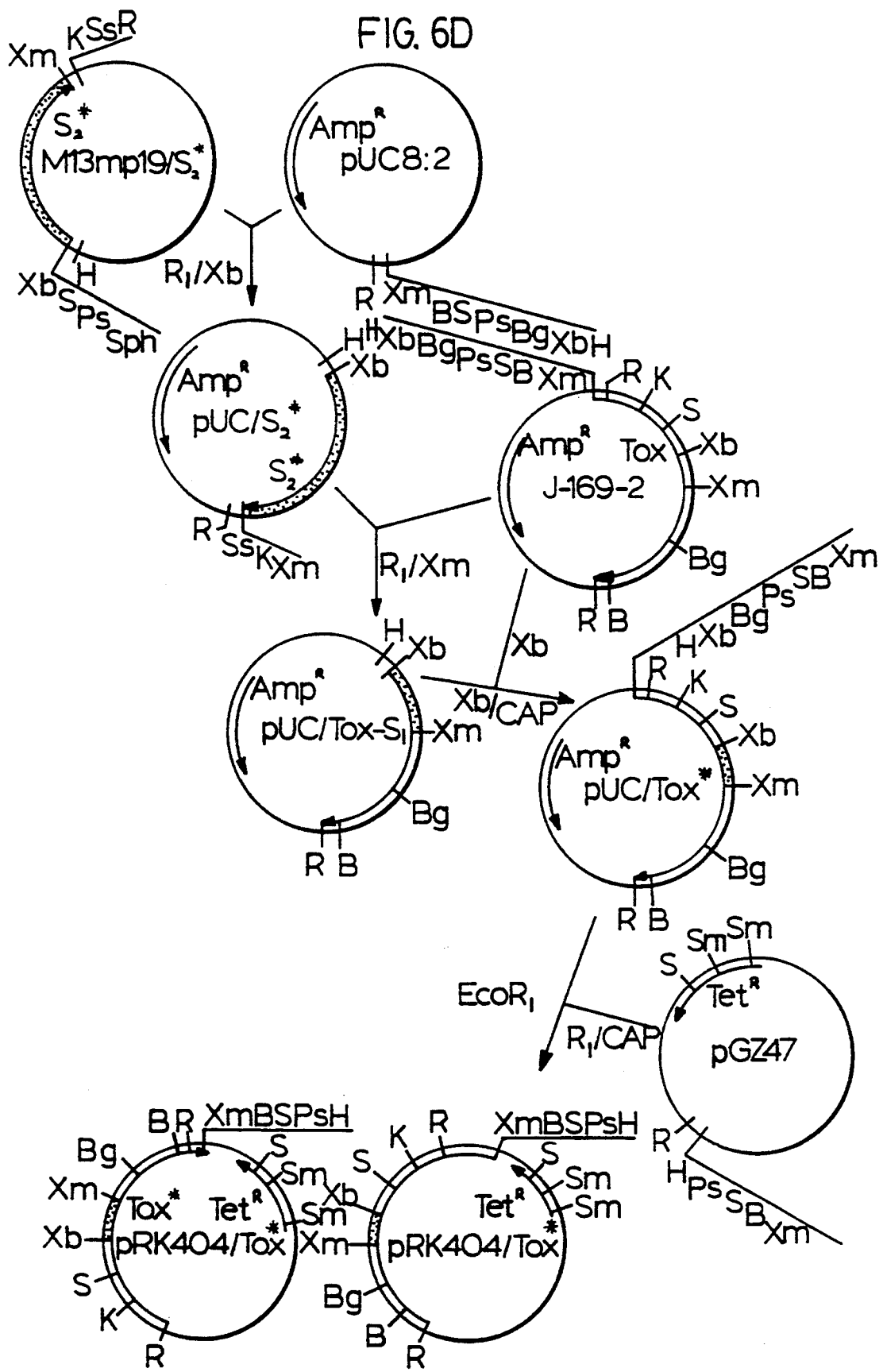

It has been shown that the TOX operons from different strains of B. pertussis are nearly identical in sequence (Nicosia et al, Proc. Nat. Acad. Sci., U.S.A., 83, 4631, [1986]; Locht & Keith, Science, 232 1258, [1986]). The TOX locus is here defined as a 4.7 kb DNA fragment beginning at the EcoR I cleavage site which encodes a 5'-flanking sequence, the promoter region, the structural genes for all PT subunits and a 3' flanking sequence. The TOX gene from B. pertussis 10536, which is the strain used by the inventors, was cloned and sequenced. Its nucleic acid sequence was found to be highly homologous to other published sequences, with four unique base differences downstream from the G of the EcoR I site defined as base 1. The complete nucleotide and corresponding amino acid sequences of the structural genes are shown in FIGS. 5(i)–5(iii).

The plasmid DNA of clone J-169-1 which contains the TOX gene from Bordetella pertussis 10536 cloned into pUC8:2 as a 4.7 kb EcoR I fragment, has been deposited with the American Type Culture Collection (ATCC) in Rockville, Md., U.S.A. on Nov. 23, 1988 under Accession Number 40518.

The T at position 315 is unique to strain 10536 and there are three differences in the S1 gene at positions 710, 1200 and 1202, resulting in two unique amino acids, glutamic acid and valine, at positions 34 and 198 of the mature S1 sequence, respectively. The toxin genes of B. parapertussis and B. bronchiseptica are not expressed because of multiple mutations in their promoter regions, (Arico & Rappuoli, J. Bacteriol., 169, 2849, [1987]). This has allowed the use of B. parapertussis as a host for the expression of mutated toxin genes for screening purposes.

The inventors have shown that substitution of a single amino acid in S1, in particular at the active site for NAD hydrolysis (position 129), virtually abolishes the ADP-ribosyltransferase activity of PT. The inventors determined the importance of the GLU$^{129}$ site by experiment, as set forth below. However, it may be desirable to alter several sites on the holotoxin to ensure complete safety. Accordingly, this invention applies to single or multiple mutations in both or either of the A and B portions of the holotoxin to abolish toxicity, and to the reinsertion of these mutations back into the genome of Tox$^-$ strains of Bordetella.

A number of strategies have been used by the inventors to determine regions of the holotoxin that might be closely associated with its biological activities, and might, therefore, contain candidate sites for genetic manipulation.

PT was prepared from culture supernatants of B. pertussis (strain 10536). The crude solution was concentrated by ultrafiltration and passed through a fetuin-agarose affinity column to adsorb PT. PT was eluted from the washed column using potassium thiocyanate and dialyzed into a phosphate-saline medium. At this stage, the purity was 90–95%, as determined by sodium dodecyl sulphate - polyacrylamide gel electrophoresis (SDS-PAGE) analysis. The major contaminant was FHA. Further purification was achieved by chromatography through a hydroxylapatite column, giving a material with a purity >99%.

The site of interaction of the S1 subunit with NAD was determined by photo-crosslinking NAD to isolated and purified S1 using [$^{14}$C]NAD, labelled either in the nicotinamide carbonyl group or the adenine moiety. Radiolabel was efficiently transferred from the nicotinamide moiety into the protein. The protein then was digested with trypsin and chromatographed on an HPLC column, giving two major radioactive peptides. After purification, the two tryptic peptides were sequenced which demonstrated that the first fifteen residues corresponded to residues 118 to 132 of mature S1. In both peptides, radioactivity was associated with an unidentified amino acid corresponding to position 129 in mature S1. Radioactivity was not detected in any other position. This established that GLU$^{129}$ is the site of photo-crosslinking of NAD and, therefore, is likely to be an important component of the nicotinamide interaction site. Significantly, the sites of linkage in diphtheria toxin and P. aeruginosa exotoxin A are also glutamic acid residues and the three amino acid sequence commencing at GLU$^{129}$ of S1 resembles the analogous sequences of the other bacterial toxins.

Chromosomal DNA was prepared from B. pertussis (strain 10536) and was digested with the restriction enzyme EcoR I in such a way that fragments were obtained ranging in size from a few hundred bases to a few kilobases. The DNA fragments were ligated with λ gt11 DNA which had been digested with EcoR I and dephosphorylated. The DNA was packaged into phage particles and maintained in E. coli Y1090 as a λ gt11 B. pertussis genomic library. Alternatively, B. pertussis chromosomal DNA was digested with the restriction enzyme Sau3A I to generate very large DNA fragments which were ligated with BamH I restricted λ Charon 35 DNA. The DNA was packaged into phage particles and maintained in *E. coli* LE392 as a λ Ch 35 *B. pertussis* genomic library.

These genomic libraries were plated and phage plaques transferred onto nitrocellulose filters. The filters were screened by DNA hybridization using an oligonucleotide probe specific for the PT S4 subunit. Positive plaques were further purified by two additional rounds of plating and hybridization. Phage DNA was prepared from the positive plaques and subjected to restriction enzyme digestion and Southern blot analysis. Clones containing the entire 4.7 kb EcoR I pertussis toxin operon (TOX) or portions thereof and with differing 5'- or 3'-flanking regions were characterized. The TOX gene was subcloned for sequence analysis and further genetic manipulation. Sequencing was performed using the dideoxy chain termination method and the results indicated four novel bases in the 10536 TOX gene as compared to published sequences.

Subclones of S1 or S3 genes in M13 phage were subjected to in vitro site-directed mutagenesis using the phosphorothioate procedure. Single-stranded DNA from these clones was annealed with oligonucleotide primers specifically designed to mutate or delete one or more amino acids. The mutagenesis was carried out using a kit available from a commercial source. Mut at ions were verified by sequencing of single-stranded phage DNA. Mutant subunit genes were recombined with the remainder of the operon to construct mutant holotoxin genes in the broad-host-range plasmid pRK404 maintained in *E. coli* JM109.

In order to characterize the holotoxin analogues, these plasmids were transferred to a spontaneous streptomycin-resistant *B. parapertussis* strain by conjugation on a solid surface, using pRK2013 as a helper plasmid. The colonies were selected on streptomycin and tetracycline-containing Bordet-Gengou blood plates. Mutated genes also were integrated into the chromosome of *B. parapertussis* by conjugative transfer of a suicide plasmid. The integration was either random or directed through homologous recombination utilizing the flanking regions of the *B. pertussis* TOX operon. FIG. 7 shows the construction of a suicide plasmid containing mutants for random recombination.

Liquid cultures were grown in modified Stainer-Scholte medium containing methyl-β-cyclodextrin in shake flasks (10 ml to 2 L) or in fermentors (20 L to 50 L). The expression level of holotoxin analogues in culture supernatants was determined by enzyme-linked immunosorbent assay (ELISA) and found to vary with the mutation. The residual toxicity of the analogues was measured by the CHO cell clustering assay.

A number of PT analogues were purified from 2 L to 50 L cultures of recombinant *B. pertussis* strains, according to methods described in detail for native PT. The ADP-ribosyltransferase activity of these mutants was determined as the extent of incorporation of radioactivity into bovine transducin from [$^{32}$p]-labelled NAD. Table 1a below lists the PT mutants generated and Table 1b below summarizes their residual toxicity and enzymic activity.

Selected purified mutants were tested in mice for acute toxicity, histamine sensitization activity and potency in the standard mouse intracerebral challenge test. These results are presented in Table 2 below and show that PT analogues have a markedly-decreased acute toxicity and histamine sensitization activity and that they are immunoprotective in the mouse potency test.

The immunological properties of PT analogues were further investigated by epitope mapping and by analysis of the antibody response in mice. Several monoclonal antibodies (MAbs) specific for individual subunits or dimers of PT were prepared and used to determine by ELISA whether the epitopes defined by these antibodies were affected by the mutations. The S1 epitope recognized by MAb PS21 is of particular significance, since it is immunodominant in mice and this antibody confers passive protection in the mouse intracerebral challenge test. (The hybridoma which secretes the monoclonal antibody PS21 has been deposited with ATCC on Nov. 30, 1989 under accession number HB10299). The preservation of this epitope in the PT analogues is indicated in Table 1b.

Immunogenicity studies in mice were performed on three purified PT mutants. Immune sera were tested for their ability to inhibit PT-induced CHO cell clustering (Table 3 below), and for their anti-PT, anti-SI and anti-B-oligomer antibody titres by indirect ELISA (Table 4 below).

To generate a *B. pertussis* strain expressing a mutated TOX gene suitable for vaccine production, the endogenous TOX operon was deleted by homologous recombination using electroporation of linear *B. pertussis* DNA containing the 5'- and 3'-flanking regions of the TOX locus. Selected mutant holotoxin genes were then reintegrated into the TOX locus of the *B. pertussis* chromosome. Clones containing mutated TOX genes were grown and the culture supernatants assayed for level of expression of PT analogues and their residual toxicity as previously described. These results are shown in Table 5 below.

Certain *Bordetella pertussis* strains wherein the TOX gene has been removed entirely or has been replaced by certain mutant holotoxin clones, have been deposited with ATCC on Nov. 23, 1988, as follows:

| Strain | Holotoxin Modification | ATCC Accession Number |
|---|---|---|
| B. Pertussis 29-9 | TOX deleted (Tox$^-$) | 53838 |
| B. pertussis S-2962-1-2 | S1:GLY$^{129}$ | 53837 |
| B. pertussis S-2962-2-1 | S1:GLN$^{129}$ | 53836 |
| B. pertussis S-3036-2 | S1:GLU$^{58}$ | 53835 |
| B. pertussis S-3122-3-1 | SA:ALA$^{41}$ | 53834 |
| B. pertussis S-3122-2-3 | S1:GLY$^{129}$ S3:ASN$^{92}$ARG$^{93}$ | 53833 |

Other strains of *Bordetella pertussis* expressing mutant PT strain analogues have been deposited with ATCC on Nov. 30, 1989 as examples of strains which do not contain an antibiotic resistance marker, as follows:

| Strain | TOX Allele | ATCC Accession Number |
|---|---|---|
| B. pertussis str.29 | Wild Type | 53972 |
| B. Pertussis 29-8 | TOX$^-$ | 53973 |
| B. pertussis 689-169 | Gly 129 I | 53974 |
| B. pertussis 989-56 | Lys 9 Gly 129 | 53975 |
| B. pertussis 889-48 | Gly 129 I/S3 (91–93) deleted | 53976 |

The Tox⁻ strain 29-9 is a novel strain of *Bordetella pertussis* from which the toxin operon has been removed and from which foreign DNA is absent and which is capable of being grown in the absence of antibiotics to produce *B. pertussis* antigens free of pertussis toxin.

Each of the transformed strains is a strain of *Bordetella pertussis* in which the toxin operon has been replaced by a mutant gene formed by site-directed mutagenesis of at least one specific amino acid residue in the holotoxin responsible for pertussis toxin toxicity.

The data presented herein demonstrate that the inventors have produced a series of pertussis holotoxin analogues that exhibit a substantial reduction in CHO cell clustering and enzymic activities (0.0001 to 1% of the wild-type activity). Many of these analogues also maintain an immunodominant S1 epitope recognized by a protective monoclonal antibody. Moreover, certain of these mutants have been shown to protect mice against challenge with virulent *B. pertussis* at doses that exhibit minimal toxicity. While the majority of these results have been generated using PT mutants secreted by *B. parapertussis*, it is evident that equivalent products are obtained by genetic manipulation of *B. pertussis* itself. Other Bordetella species of the same general configuration, namely *B. bronchiseptica* and *B. avium*, also may be used as hosts for the mutated holotoxins. This disclosure, therefore, presents a number of detoxified immunogenic and immunoprotective forms of pertussis holotoxin that are candidates for inclusion in a novel pertussis vaccine, and a method for producing them in Bordetella species, including *B. pertussis*.

The mutated immunoprotective pertussis holotoxin may be combined with other immunoprotective materials to form a multivalent vaccine against two or more diseases, including pertussis and diphtherin, tetanus, polio and/or haemophilus b.

In addition, the pertussis holotoxin may be combined with other pertussis antigens in a multi-component vaccine.

Further, the modified *B. pertussis* stains may be used to provide a whole cell vaccine of decreased toxicity by growing the strain in cell culture and killing the pertussis strain to provide the vaccine.

Plasmid DNA necessary to generate recombinant *B. pertussis* strains containing other mutated TOX alleles has been deposited with ATCC on Nov. 30, 1989 as follows:

| Plasmid | TOX Allele | ATCC Accession Number |
| --- | --- | --- |
| J-229-17 | Wild Type | 40715 |
| S-3319-3-9 | Gly 129 I | 40716 |
| S-3421-1-23 | Glu 58 Gly 129/S3 (91 to 93) deleted | 40718 |
| S-3501-2-4 | Lys 9 Glu 58 Gly 129 II | 40717 |

The deposits made with ATCC referred to herein have been made under the terms of the Budapest Treaty. Upon the issuance of a patent on this United States patent application, the biological materials will be irrevocably and without restriction or condition released to the public.

EXAMPLES

Methods of molecular genetics, protein biochemistry and fermentation and hydridoma technology used but not explicitly described in this disclosure and these Examples are amply reported in the scientific literature and are well within the ability of those skilled in the art.

EXAMPLE I

This Example illustrates the preparation and purification of PT.

Culture supernatants of *B. pertussis* (strain 10536) were concentrated 20 to 50 times by ultrafiltration through a 10,000 or 20,000 molecular weight cut-off membrane using a Millipore Pellicon cassette system. The toxin was adsorbed from crude concentrates by passage through a fetuin-agarose affinity column equilibrated with 1 M potassium phosphate, 10 mM NaCl at pH 7.5. The volume of adsorbent was typically 1 ml per mg of toxin. The loaded column was washed with 100 mM potassium phosphate, 1 M NaCl at pH 7.5, then eluted with the same buffer containing 3 M potassium thiocyanate to desorb the toxin. Pooled fractions were dialyzed against 50 mM Tris-HCl 200 mM NaCl containing 10% v/v glycerol at pH 8.0, to remove thiocyanate, then against 50 mM Tris-HCl, 200 mM NaCl containing 50% v/v glycerol at pH 8.0, to allow storage of the product at $-20°$ C. The yield as determined by ELISA was typically 90 to 95%. The purity as determined by SDS-PAGE was 90 to 95%, the major contaminant being FHA. For further purification, the stored toxin was diluted five-fold with water and loaded onto a hydroxylapatite column of volume 1 ml per mg of toxin, that had been equilibrated with 10 mM potassium phosphate at pH 8.0. The column was washed with 30 mM potassium phosphate at pH 8.0 and then eluted with 100 or 200 mM potassium phosphate to desorb the toxin. Pooled fractions were dialyzed against 100 mM potassium phosphate containing 50% v/v of glycerol at pH 8.0 and the final product stored at $-20°$ C. The yield was typically 90 to 95%, and the purity $>99\%$ as shown by SDS-PAGE.

EXAMPLE II

This Example illustrates the preparation of PT subunit S1.

PT was adsorbed to fetuin-agarose as described in Example I, then the column was washed with CHAPS buffer (500 mM urea, 50 mM potassium phosphate, 100 mM NaCl and 1% w/v of CHAPS(3-[(3-cholamidopropyl)-dimethylammonio]-1-propanesulphonate) at pH 7.5). The column was eluted with the same medium containing 500 $\mu$M of adenosine triphosphate (ATP). The S1 subunit emerged as a sharp peak at the column volume. The pooled fractions were passed through a clean fetuin-agarose column equilibrated with CHAPS-/ATP buffer to remove residual B oligomer, then dialyzed against 100 mM potassium phosphate containing 50% v/v glycerol at pH 8.0 for storage at $-20°$ C. S1 was quantified by reverse-phase HPLC on a Vydac C4 column by comparison of the integrated peak area with that of a PT standard. The yield was typically only 20 to 25%, but the product was free of other subunits as demonstrated by both SDS-PAGE and reverse-phase HPLC.

EXAMPLE III

This Example illustrates the photocrosslinking of NAD to the S1 subunit.

Reaction mixtures (100 $\mu$l) containing 50 $\mu$g/ml of S1, 10 mM dithiothreitol and 50 $\mu$M NAD in CHAPS buffer were placed in the wells of a 96-well microtitre plate set in ice, preincubated for 30 min and then irradiated at 254 nm for periods up to 3 hr at a distance of 5 cm with a 9 W mercury lamp. Samples were then assayed for residual NAD glycohydrolase activity. The enzyme activity of S1 was completely abolished after irradiation for 2 hr, whereas the extent of photoinactivation was only 40% under the same conditions but in the absence of NAD. This result indicated that NAD dependent photochemical events had occurred. To discover which part of the NAD molecule interacted with the protein and the extent of crosslinking, S1 was irradiated under identical conditions with [carbonyl-$^{14}$C]NAD or [adenine-$^{14}$C]NAD. Aliquots were removed at intervals up to 3 hr and treated with trichloroacetic acid (TCA) to 10% w/v. The precipitated protein was collected by filtration, washed with fresh 10% w/v TCA and counted in a scintillation counter. Results indicated that the radiolabel was incorporated from the nicotinamide moiety rather than from the adenine moiety, and that the extent of incorporation was 0.75 mol label per mol protein.

EXAMPLE IV

This Example identifies the site of photocrosslinking on the S1 subunit.

Reaction mixtures (3 ml) containing 100 μg/ml of S1, 10 mM dithiothreitol and 50 μM [carbonyl-$^{14}$C]NAD in CHAPS buffer were placed in a Petri dish on ice to give a 1 mm layer, and then irradiated at 254 nm for 2 hr with gentle magnetic stirring. The solution was deaerated with nitrogen, further reduced with dithiothreitol and S-alkylated with 4-vinylpyridine to prevent oxidation of thiol groups. The reaction mixture was dialyzed extensively against 10 mM acetic acid and the radiolabelled protein was collected after precipitation with 20% w/v TCA.

The precipitated protein (1 mg) was redissolved in 2 M urea, 200 mM ammonium bicarbonate to 500 μg/ml and digested with 50 μg/ml trypsin for 20 hr at 37° C. The mixture was acidified and fractionated on a 1×25 cm Vydac $C_{18}$ reverse-phase HPLC column, using a linear gradient of 0 to 50% acetonitrile in 10 mM trifluoracetic acid (TFA). Fractions were checked by scintillation counting, which revealed two major radioactive peptides, denoted A and B, accounting for 50% of the eluted radioactivity. The peptide pool was lyophilized, redissolved in 10 mM TFA, 6 M guanidinium chloride and separated on a Vydac CI8 column using a 20 to 30% acetonitrile gradient in 10 mM TFA. Each peptide was further purified to homogeneity on the same column by applying an acetonitrile gradient in 20 mM ammonium acetate at pH 6.5, and the solutions evaporated to dryness. Their specific radioactivities were consistent with only one labelled site per molecule.

The two peptides were sequenced by automated Edman degradation. A portion of the sequenator effluent was diverted for monitoring of radioactivity. The results are shown in FIG. 1. Up to cycle 15, the sequences proved to be identical and correspond unequivocally to residues 118 to 132 of mature S1. In both peptides, radioactivity was associated with an unidentified amino acid released at cycle 12, corresponding to position 129 in mature S1. No radioactivity was detected at cycles beyond 15. Thus it was established that GLU$^{129}$ was the site of crosslinking, and was therefore likely to be an important component of the nicotinamide interaction site.

EXAMPLE V

This Example illustrates the preparation of *B. pertussis* chromosomal DNA.

Two liters of *B. pertussis* (strain 10536) were grown in modified Stainer-Scholte medium as 16×125 ml aliquots using a 4 ml inoculum of saturated growth for each flask. This medium consists of L-proline 5 g/L, NaCl 2.5 g/L, $KH_2PO_4$ 0.5 g/L, KCl 0.2 g/L, $MgCl_2.6H_2O$ 0.1 g/L, Tris 1.5 g/L, casamino acids 10 g/L, methyl-β-cyclodextrim 2 g/L, $CaCl_2.2H_2O$ 0.02 g/L, mono-sodium glutamate 10 g/L, L-cysteine 0.004%, $FeSO_4.7H_2O$ 0.001%, niacin 0.004%, glutathione 0.015%, and ascorbic acid 0.04%, pH.7.6. Samples were grown in 500 ml flasks, on a shaker at 35° to 36° C., 150 rpm for 16.5 hr to log phase. The cells were spun in 500 ml aliquots at 5000 xg for 1 hr at 4° C. Each aliquot was washed with 25 ml TE buffer (10 mM Tris-HCl, 1 mM EDTA, pH 7.5,) and then resuspended in 20 ml TE and frozen at −70° C. One pellet was resuspended in 90 ml TE and pronase added to 500 ug/ml. SDS was added to 1% and the sample incubated at 37° C. for 21.5 hr generating a clear lysate. The lysate was extracted with 1 volume of phenol saturated Tris-HCl at pH 7.5 at room temperature for 2 hr, with gentle agitation. The phases were separated by centrifugation at 2800 xg for 15 min at 20° C. and the aqueous phase extracted similarly with 1 volume of 1:1 phenol:-chloroform. The phases were separated by centrifugation at 2100 xg for 10 min at 20° C. and the aqueous phase extracted with chloroform for 2 hr as described. The phases were separated by centrifugation at 1600 xg for 5 min at 20° C. and the aqueous phase subjected to dialysis at 4° C. against 2 L of 1 M NaCl for 24 hr with one change of buffer, then against 2 L TE for 48 hr with one change of buffer.

EXAMPLE VI

This Example illustrates the generation of *B. pertussis* gene libraries.

1) λ gtll EcoR I library

*B. pertussis DNA* (10 μg) was digested with EcoR I (10 units) in the presence of 100 mM Tris-HCl pH 7.5, 50 mM NaCl, 5 mM $MgCl_2$, 100 μg/ml BSA, 1 μg/ml RNAse A for various lengths of time in order to generate a set of partially digested DNA fragments. At each time point of 0.25, 0.5, 1, 2, 4 and 8 hrs, the sample was placed at 0° C. and EDTA added to 20 mM to stop the reaction. The samples were pooled and separated on a 10 to 40% sucrose gradient in TNE (20 mM Tris-HCl, pH 8.0, 5 mM EDTA, 1 M NaCl) at 85,000 xg for 20 hr at 20° C. The gradient was fractionated from the top as 24 aliquots (0.5 ml) to which 1 ml aliquots of absolute ethanol were added to precipitate the DNA. The samples were incubated on dry ice for 30 min and then centrifuged at 12,000 xg for 5 min at 4° C. The pellets were washed with 750 μl of 70% ethanol, incubated on dry ice for 5 min, centrifuged at 12,000 xg for 5 min, and then dried. Each pellet was resuspended in 25 ul of sterile water and 5 μl aliquots of every alternate fraction were submitted to agarose gel electrophoresis to determine the size of the fragments. Samples containing DNA ranging in size from approximately 0.5 kb to 9 kb were pooled. The pooled EcoR I-digested *B. pertussis* DNA (0.4 μg) was ligated with EcoR I-digested, dephosphorylated λ gtll DNA (0.5 μg) and was packaged into phage particles using a commercial kit. The phage library was propagated in *E. coli* Y1090 cells and was titred at approximately $10^{10}$ plaque-forming units(pfu)/μg of λ gt11 DNA. The library was amplified to $4 \times 10^{10}$ pfu/ml for screening clones. The amplification was performed on plates by growing cells to saturation overnight in media containing 0.2% maltose, then adding $10^4$ to $10^5$ pfu of library per 0.6 ml of cells and allowing the phage to adsorb to the cells for 15 min at 37° C. The sample was mixed with soft agar, plated, and incubated overnight at 37° C. The soft agar/cells/phage layer was scraped from the confluent plates which were washed with 4 ml SMG buffer (0.4 M NaCl, 10 mM MgSO4, 50 mM Tris-HCl, pH 7.5, 0.01% gelatin). The wash and phage agar were combined, 100 μl of chloroform added, and the mixture incubated at 37° C. for 15 min with gentle agitation. The sample was centrifuged at 4000 xg at 4° C. for 10 min twice to obtain a clear supernatant. Chlorofom was added to a final concentration of 0.3% and the library stored at 4° C.

2) λ Charon 35 Sau3A I library

B. pertussis DNA ($3 \times 166$ ug) was digested with Sau3A I ($3 \times 220$ units) in the presence of 10 mM Tris-HCl pH 7.5, 100 mM NaCl, 10 mM MgCl2, 100 μg/ml BSA for 1 min, 2 min, or 3 min in order to generate very large fragments of DNA. After each reaction, EDTA was added to 20 mM and then 2.5 volumes of absolute ethanol added to precipitate the DNA as described above. The DNA was resuspended in TNE and separated on a 10 to 30% sucrose in gradient in TNE, as described above. Fractions were taken as before and the DNA fragment sizes visualized by agarose gel electrophoresis. λ Charon 35 DNA ($2 \times 50$ ug) was ligated to generate a circularized form before being digested with BamH I ($2 \times 20$ units) in the presence of 150 mM NaCl, 6 mM Tris-HCl pH 7.9, 6 mM MgCl2, 100 ug/ml BSA to remove the stuffer fragments. The lambda arms were purified by pelleting through an 8 to 20% potassium acetate gradient at 85,000 xg, for 16 hr at 32° C. The Sau3A I digested DNA was ligated with the lambda arms at 6° C. for 72 hr, then packaged into phage using a commercial kit. The phage library was propagated in E. coli LE392 cells and was titred at approximately $1 \times 10^5$ pfu/μg of lambda arms. The library was amplified to 1 to $2 \times 10^{10}$ pfu/ml for screening as described above.

EXAMPLE VII

This Example illustrates the screening of the B. pertussis libraries.

1) λ gt11 genomic library

A 30-base oligonucleotide probe was synthesized based on the nucleotide sequence of the gene encoding PT subunit S4. The DNA was purified from urea/acrylamide gels by uv-imaging and anion exchange chromatography on Whatman cellulose DE52. The sequence of the oligonucelotide was 5'GTAGCCATGAAGCCGTATGAAGTCACCCCG3', coding for amino acids 16 to 25 of the mature S4 protein. The oligonucleotide was 5' end-labelled in a reaction mix containing 10 ug DNA, 25 uCi [α-$^{32}$P]ATP ,4 units polynucleotide kinase in the presence of 50 mM Tris-HCl, pH 9.5, 10 mM MgCl2, 5 mM DTT, 5% glycerol by incubation at 37° C. for 15 min. ATP was added to 1.5 mM and the incubation continued for 1.75 hr at 37° C. 10 ug of tRNA were added as carrier and the labelled DNA was separated from free ATP on a Sephadex G50 superfine column eluted with 0.1 M triethylammonium bicarbonate, pH 7.6. Peak fractions were pooled and lyophilized to dryness. The pellet was washed with sterile water, relyophilized and then resuspended at approximately 0.1 μg/μl.

Aliquots of the λ gt11 B. pertussis genomic library were plated on a Y1090 lawn on NZCYM plates containing 0.2% maltose. Plaque-lifts were made onto nitrocellulose filters, which were sequentially treated with denaturing solution (1.5 M NaCl, 0.5 M NaOH) for 1 min, neutralizing solution (1.5 M NaCl, 0.5 M Tris-HCl pH 8.0) for 5 min, and rinsed briefly in 2xSSPE (0.36 M NaCl, 20 mM sodium phosphate, pH 7.4, 2 mM EDTA) before being baked at 80° C. under vacuum for 2 hr to fix the DNA. Nitrocellulose filters were subsequently incubated in a prehybridization buffer comprising 5xSSC (0.75 M NaCl, 75 mM sodium citrate, pH 7.5), 5x Denhardt's mixture (0.1% Ficoll 400, 0.1% polyvinylpyrrolidone, 0.1% BSA), 0.1% SDS, 100 μg/ml herring sperm DNA for 2 hr at 45° C. The prehybridization buffer was removed and fresh buffer containing $10^7$ cpm of [$^{32}$P]-labelled oligonucleotide probe was added. Hybridization was carried out at 45° C. for 16 hr. The radioactive solution was removed and the filters rinsed briefly twice at room temperature with 5xSSC, 0.1% SDS to remove unbound probe. The filters were further washed twice with 5xSSC, 0.1% SDS for 1 hr at 50° C. and then air-dried and subjected to autoradiography.

The plaque-containing plates were aligned with their autoradiograms and putative positive plaques were subjected to another two rounds of purification on plates. One clone (λ gt11-15-4-1) was chosen for detailed examination by Southern blot analysis.

2) λ Charon 35 genomic library

Aliquots of the λ Charon 35 B. pertussis genomic library were plated on an LE392 lawn on NZCYM plates containing 0.2% maltose. The plaque-lift, hybridization and washing protocols were performed as described above. Positive plaques were purified twice more on plates and several clones, λ Ch 35 111, 121, 411, 421 and 431, were examined by Southern blot analysis.

EXAMPLE VIII

This Example illustrates the analysis of the genomic clones.

1) Preparation of phage DNA

One liter ($2 \times 500$ ml) of phage culture was prepared. LE392 or Y1090 cells were grown overnight in medium containing 0.2% maltose. Cells ($10^{10}$) were spun down at 4400 xg for 5 min at 4° C. and the pellet resuspended in 1 ml SMG buffer. Phage stock ($1.2 \times 10^8$ pfu) was added to the mixture and incubated at 37° C. for 15 min to absorb the phage to the cells. The phage/cell mixture was inoculated into 500 ml of medium and the culture shaken vigorously at 37° C. until lysis began (4–4.5 hr) . Chloroform (10ml) was added and shaking continued at 37° C. for an additional 15 min to complete the lysis. The sample was cooled to room temperature and DNase I and DNase-free RNase A (1 μg/ml each) were added for 30 min at room temperature. The cell debris was pelleted at 3500 xg for 20 min, then 29.2 g NaCl and 50 g polyethylene glycol (PEG 6000) were added to 500 ml of supernatant. The sample was gently agitated at room temperature to dissolve the solids, then incubated at 0° C. for 1 to 2 hr to precipitate the phage. The phage were harvested by centrifuging at 4400 xg at 4° C. for 20 min and were resuspended in 8 ml TM buffer (50 mM Tris-HCl, pH 7.5, 10 mM MgSO4). Extraction with 8 ml chloroform to remove the PEG gave a clear supernatant which was applied to a step gradient of 5% and 40% glycerol in TM buffer and centrifuged at 154,000 xg at 4° C. for 1 hr. The supernatant was discarded leaving a phage pellet which was resuspended in 0.5 ml TM buffer. DNase I was added to 5 μg/ml and RNase A to 50 μg/ml and the sample incubated at 37° C. for 30 min. EDTA was added to 20 mM, pronase to 0.5 mg/ml, SDS to 0.5%, and the sample further incubated at 37° C. for 1 hr. The sample was gently extracted once each with phenol, phenol:chloroform 1:1, and chloroform and the phage DNA precipitated with ethanol.

2) Results

Clone 15-4-1 which was derived from the EcoR I λ gt11 library, was found by Southern blot analysis to contain the 4.6 kb EcoR I fragment encoding the entire TOX gene plus small 5'- and 3'-flanking regions.

The λ Charon 35 clones were found to be closely related. Some clones contained the entire TOX operon plus flanking regions in either orientation, and others did not include the entire TOX region.

The maps of clones 15-4-1, Ch 111, Ch 121/411, Ch 431 and Ch 421 are shown in FIGS. 2-2E.

EXAMPLE IX

This Example illustrates the construction of pUC-based plasmids containing the pertussis toxin operon (TOX) or portions thereof.

Phage DNA from the λ gtll clone 15-4-1 was prepared as described and digested with restriction endonuclease EcoR I using standard methods. The DNA was purified by gel electrophoresis in low-melting-point agarose. The 4.6 kb band was identified by uv-illumination of the ethidium bromide stained gel and excised. The DNA was extracted by a freeze-thaw technique employing 0.3 M sodium acetate, pH 7.0 and was precipitated with ethanol. DNA from pUC8:2, a derivative of pUC8 containing two extra restriction sites for Bgl II and Xba I in its multiple cloning site, was digested with EcoR I. The linearized DNA was dephosphorylated by standard methods using calf alkaline phosphatase (CAP), phenol extracted and precipitated with ethanol.

The pUC8:2-vector DNA and 15-4-1-derived-TOX DNA were ligated in a standard reaction and the ligation mixture used to transform competent JM109 cells according to standard procedures. The resulting colonies were analysed by a rapid DNA screening technique and two clones were chosen for large-scale preparation of plasmid DNA. These clones, J-169-1 and J-169-2, differed only in the orientation of the TOX insert. The construction of these clones is illustrated in FIG. 3.

EXAMPLE X

This Example illustrates the sequencing of the TOX operon.

1) Clones used

The clone J-169-1 was used as the source for all sequencing clones. The TOX operon was divided into five approximately equal DNA segments and was subcloned into M13mp18, M13mp19 or pUC8:2 as illustrated in FIGS. 4A, B, C, D, and E.

2) Preparation of samples

M13 clones were maintained in JM101 and DNA for sequencing was prepared from single plaques on homogeneous plates. A saturated JM101 culture was diluted 1:50 with fresh medium and infected with a single plaque. The culture was grown with vigorous shaking at 37° C. for 6 hr. The cells were removed by centrifugation and the supernatant treated with ¼ volume of 20% PEG 6000, 2.5M NaCl to precipitate phage. The suspension was centrifuged and the phage pellet was resuspended in TE, then extracted gently twice each with phenol, phenol:chloroform (1:1) and chloroform. The phage DNA was precipitated with sodium acetate and ethanol, washed with 70% ethanol and dried. The DNA was resuspended in sterile water to a concentration of about 1 μg/ml for sequencing.

Sequencing primers of approximately 17 to 20 bases were synthesized on an ABI 380A DNA synthesizer using phosphoroamidite chemistry and were purified as described above.

3) Sequencing

The dideoxy chain termination method of Sanger was used for all sequencing reactions, employing either Klenow polymerase or Sequenase T7 enzyme.

4) Results

The entire TOX operon, as previously defined, was sequenced and the result compared with published sequences. There was excellent agreement with the TOX sequence of strain BP 165 reported by Nicosia et al., except for four base differences. The T at position 315 in the 5'-flanking region is unique to *B. pertussis* strain 10536. The three other substitutions are in the S1-coding region at positions 710, 1200 and 1202 resulting in two unique amino acids, GLU34 and VAL198. The nucleotide sequence and derived amino acid sequence are shown in FIGS. 5(i)-5(iii).

EXAMPLE XI

This Example illustrates mutagenesis of the TOX gene.

1) Clones used

For mutations in the S1 gene, clone S-2403 (M13mp18/S1) was used and for the mutations in the S3 gene, clone S-2664-5-6, (M13mp18/S3(c)) was used. These clones are represented in FIGS. 4A-4E.

2) Mutagenesis protocol

Single-stranded DNA was prepared from phage stocks derived from single plaques on homogeneous plates as described previously. Mutagenic primers of appropriate sequence and length were synthesized on an ABI 380A DNA synthesizer.

Commercial kits based on the phosphorothioate procedure developed by Eckstein were used for in vitro mutagenesis. In this procedure, the mutagenic oligonucleotide was annealed to the single-stranded (wild-type) template and polymerization carried out using as substrates a phosphorothioate dCTP analogue and natural dATP, dGTP and dTTP. The double-stranded DNA was nicked with Nci I and the native strand digested with exonuclease III beyond the point of the mutation. The complementary strand was protected from Nci I-nicking by the phosphorothioate groups. The complementary strand then served as a template in a second round of polymerization, to yield double-stranded DNA with the mutation in both strands. This DNA was amplified in *E. coli*, and the mutation confirmed by sequencing.

Forty-one primary mutations were generated and an additional twenty-four were derived by constructing crosses among these. The mutation efficiency varied with the change desired. From one to six base changes and deletions of up to 15 consecutive bases were accomplished. The resulting amino acid changes are summarized in Table 1a below.

EXAMPLE XII

This Example describes the construction of plasmids for expression of mutated TOX genes in B. parapertussis and characterization of the PT analogues produced.

1) Replicating plasmids

Replicative-form DNA from M13 clones was used to reconstruct the TOX operon containing the desired mutation in pRK404. pRK404 is a derivative of pRK290, a conjugating plasmid of the pRK2 family, incompatibility group P-1. It is 10.6 kb in size, carries a tetracycline resistance (Tet$^R$) gene, and has a multiple cloning site from pUC8. The construction schemes for reintegrating S1 and S3 primary mutations into the operon are shown in FIGS. 6A–6D and the resulting clones are indicated in Table 1a below. Crossed mutations in S1 were generated using internal restriction sites, especially the unique Sal I site. A general scheme for crossed mutations in S1 is also shown in FIGS. 6A–6D and the resulting clones are indicated in Table 1a below.

2) Suicide plasmids

A conjugative but non-replicative plasmid was developed for random integration of TOX or mutated TOX into the chromosome of Bordetella species. FIG. 7 demonstrates the construction of these clones.

Plasmids of the types described in (1) and (2) above were introduced into B. pertussis by conjugation. The resulting strains were grown in shake-flasks or in a fermentor, and the culture supernatants were assayed as follows for concentration of toxin analogue by ELISA. Microtitre plates were coated with fetuin (2 ug/ml) in 0.05M potassium carbonate, pH 9.6 at 4° C. overnight in a humid environment. The plates were then washed twice with Delbecco's PBS containing 0.1% w/v Tween-20 and dried. Sample supernatants or wild-type PT were serially diluted and added to the wells, and the plates incubated for 30 min at room temperature then washed. Bound PT was detected using peroxidase-conjugated affinity-purified rabbit anti-PT antibodies.

Residual toxicity was measured by the CHO cell clustering assay, to determine the toxicity relative to native PT. Certain PT mutants were purified as described for native PT in Example I, and assayed for ADP-ribosyltransferase activity. These data are summarized in Table 1b below. Expression of the S1 epitope recognized by MAb PS21 was assessed by a modified indirect ELISA on culture supernatants. Fetuin-bound PT analogues were reacted with PS21 as the first antibody and visualized with an enzyme-conjugated affinity-purified goat anti-mouse IgG as the second antibody. The presence or absence of the S1 epitope recognized by MAb PS21 is indicated in Table 1b below.

EXAMPLE XIII

This Example illustrates the construction of plasmids for deletion and replacement of the endogenous B. pertussis TOX operon.

1) Plasmids containing TOX flanking regions a) 5'-flanking region

Figure 8A:
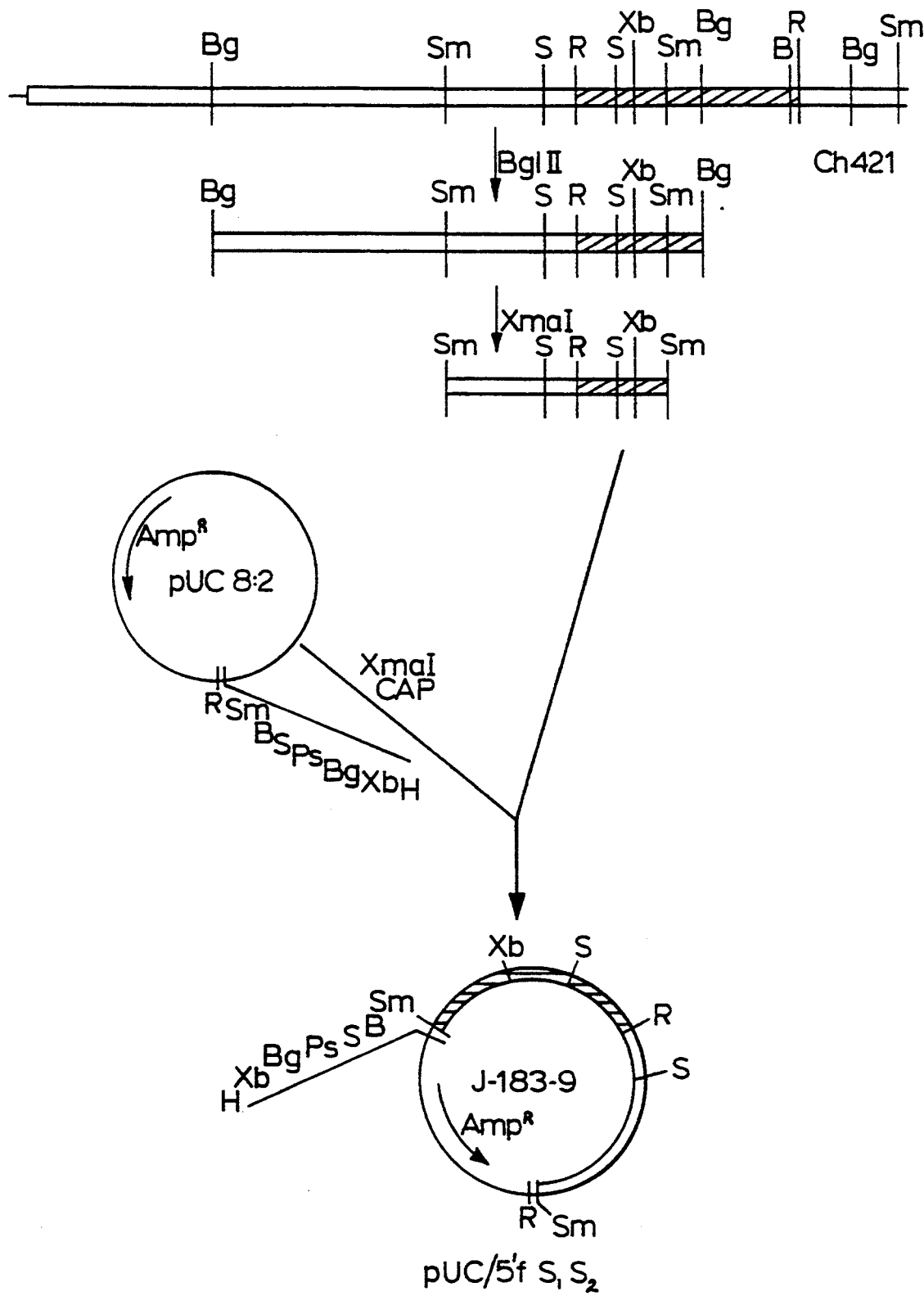

The Ch 421 DNA was first digested with Bgl II and an 11 kb fragment was purified by agarose gel electrophoresis. The Bgl II fragment was digested with Xma I and the 5 kb band subcloned into pUC8:2 previously restricted with Xma I and dephosphorylated. JM109 cells were transformed with the ligation mixture to give colonies which were analysed by a rapid DNA screening method. The clone J-183-9 was found to contain approximately 2.9 kb of the 5'-flanking region, the TOX promoter and the genes for subunits S1 and S2. FIG. 8 shows the derivation of clone J-183-9.

b) 3'-flanking region

The Ch 111 DNA was digested with Sal I and an approximately 8 kb fragment of B. pertussis DNA was gel-purified. This DNA fragment was inserted into pUC8:2 previously digested with Sal I and dephosphorylated. JM109 transformants were screened and the clone J-219-111-3 was identified as containing part of the S1 gene, all of the remaining structural genes, and about 3.9 kb of the 3'-flanking region. FIG. 8B shows the construction of this clone.

c) TOX gene with 5'- and 3'-flanking regions.

Figure 8C:
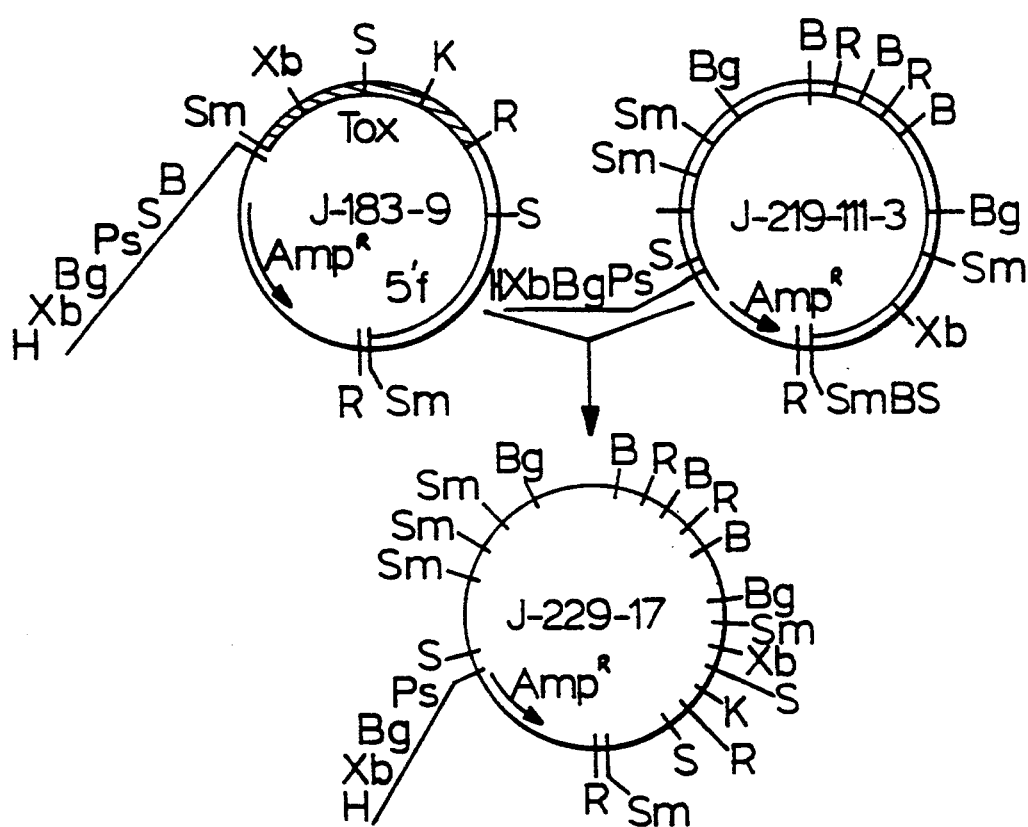

Clone J-183-9 was digested with Xba I and the approximately 7 kb fragment containing pUC8:2, the 5'-flanking region and the promoter region of the S1 gene was gel-purified and dephosphorylated. J-219-111-3 DNA was digested with Xba I and the approximately 8 kb fragment containing the structural genes for subunits S2 to S5 and the 3'-flanking regions was gel-purified. These DNA fragments were ligated and the JM109 transformants were screened to give clone J-229-17. This clone contains about 2.9 kb of the 5'-flanking sequence, the entire TOX operon, and about 4 kb of the 3'-flanking sequence. Its construction is illustrated in FIG. 8C.

d) TOX gene with 5'- and 3'-flanking regions.

Figure 11:
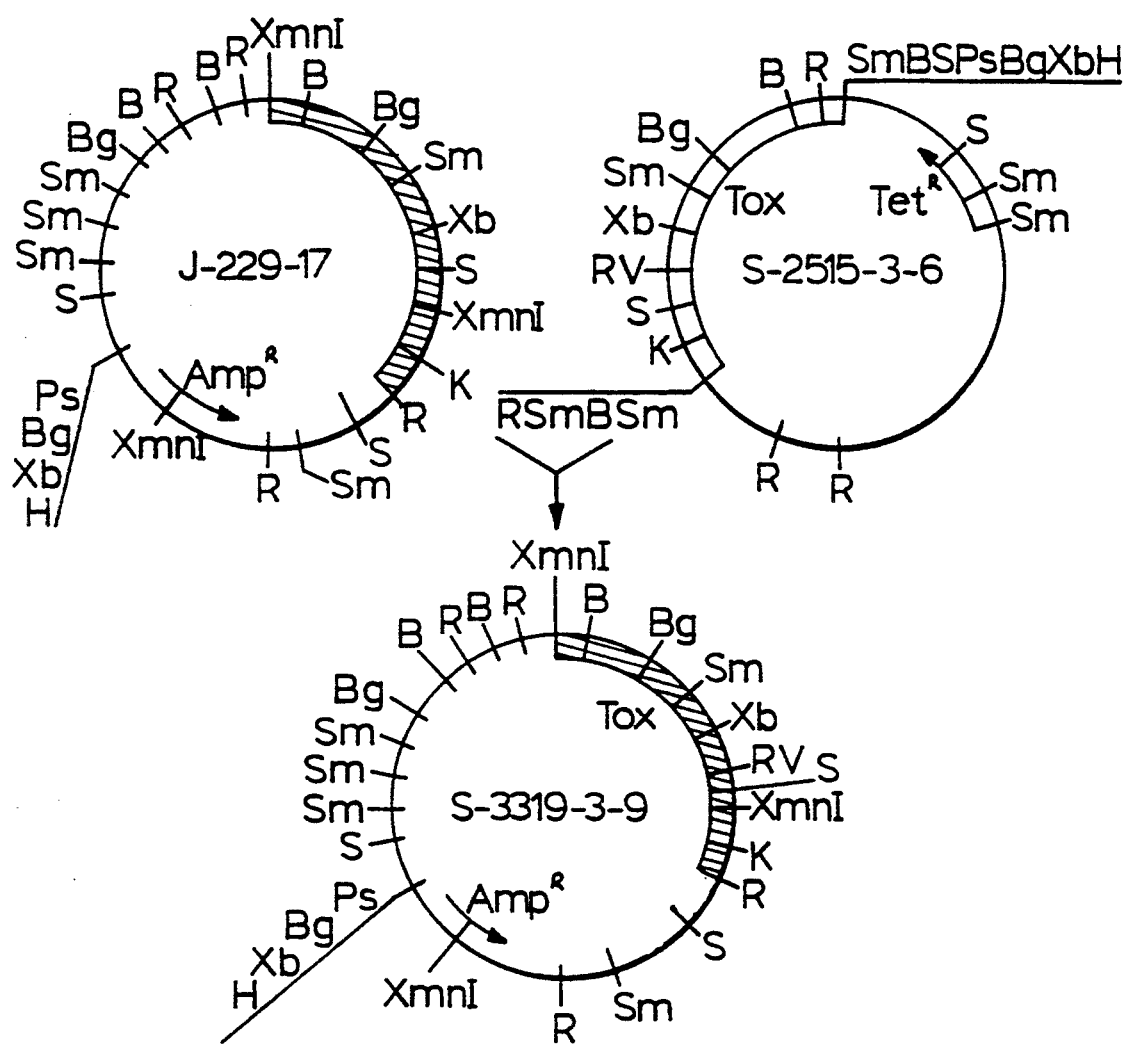
FIG. 11 shows the construction of plasmids which have been used to reintegrate the TOX analogues into the B. pertussis chromosome by homologous recombination to provide resultant B. pertussis strains which have no antibiotic resistance genes.

Clone J-229-17 (FIG. 8C) was digested with KpnI and XbaI thereby removing the fragment of DNA coding for wild-type S1. Clone S-2515-3-6, which is a pRK404/TOX Gly 129 mutant containing a unique EcoR V at the site of mutation, was used as a donor of the mutant S1 by cutting with the same enzymes. The resulting clone, S-3319-3-9, was pUC/flank/TOX Gly 129 with a new EcoR V restriction site. This clone then was used as the recipient for new mutations in S1 or the B oligomer and such mutations were analyzed for the loss of the EcoR V site. Depending on the site of mutation, new mutants were introduced by utilizing either the Xma I site or Kpn I and Xba I sites, as illustrated in FIG. 11.

2) TOX-deleting plasmids

Figure 9A:
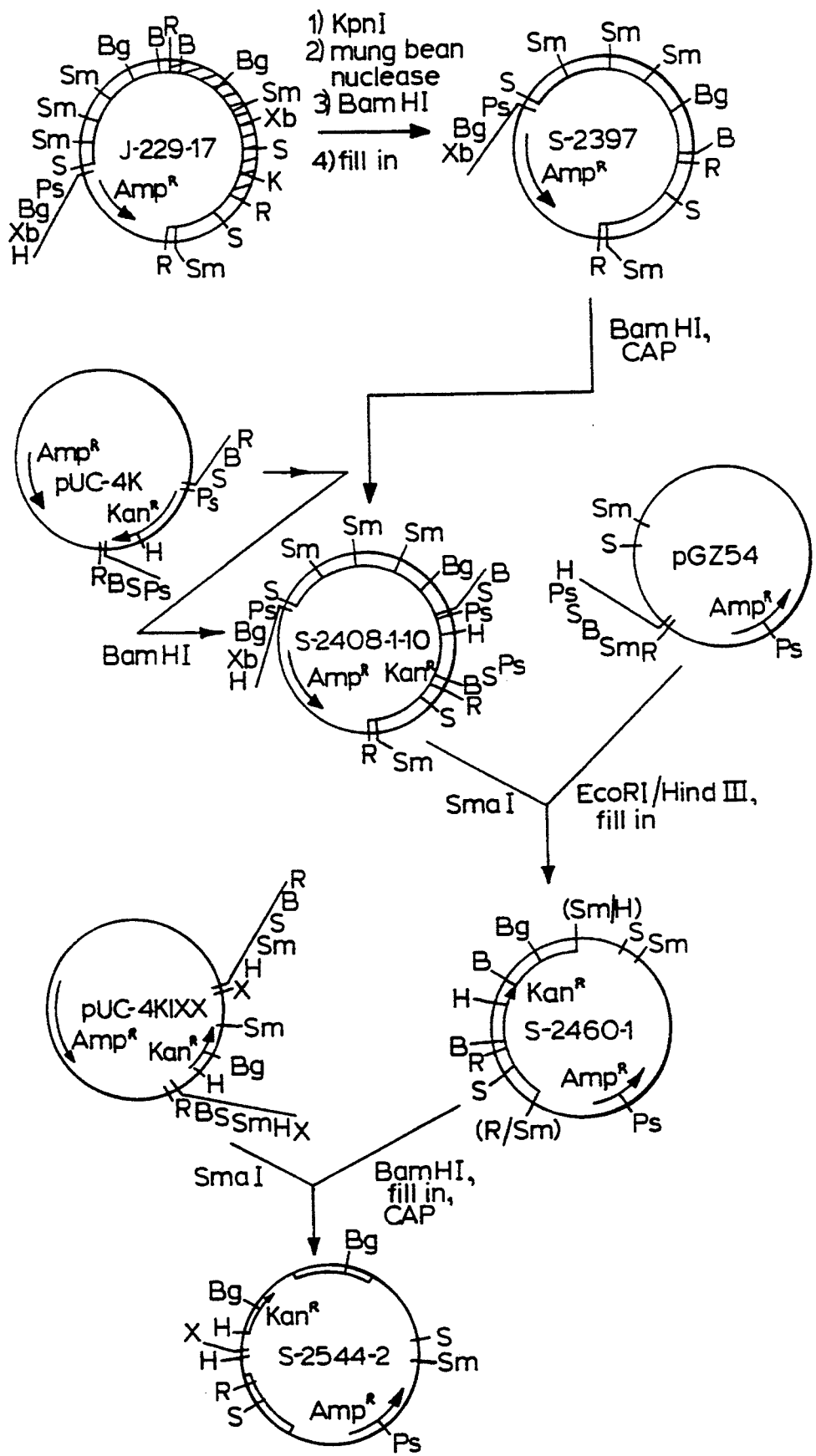
FIGS. 9A–9C show the construction of plasmids for the deletion of the TOX operon from the B. pertussis chromosome by homologous recombination.
Figure 9B:
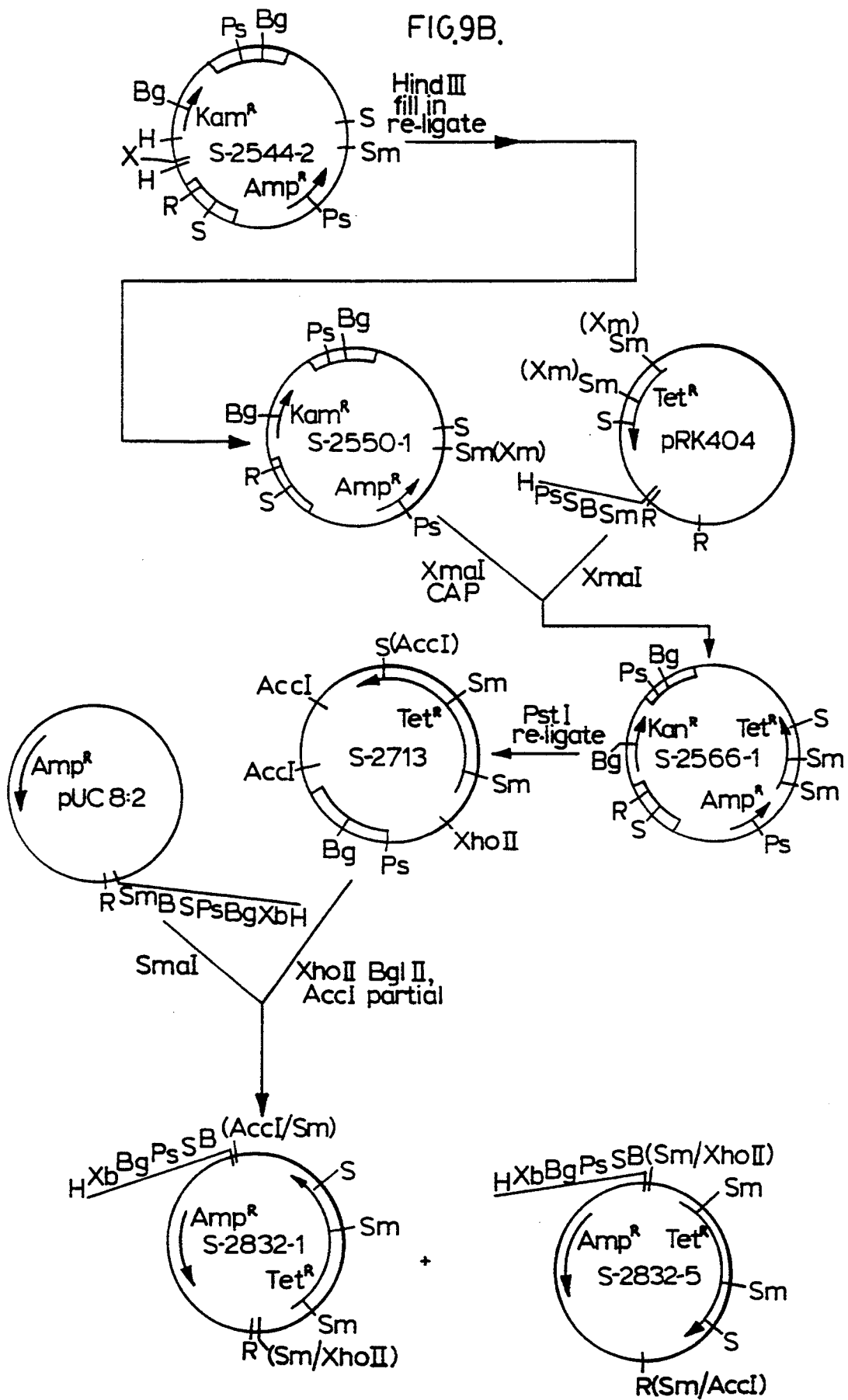
Figure 9C:
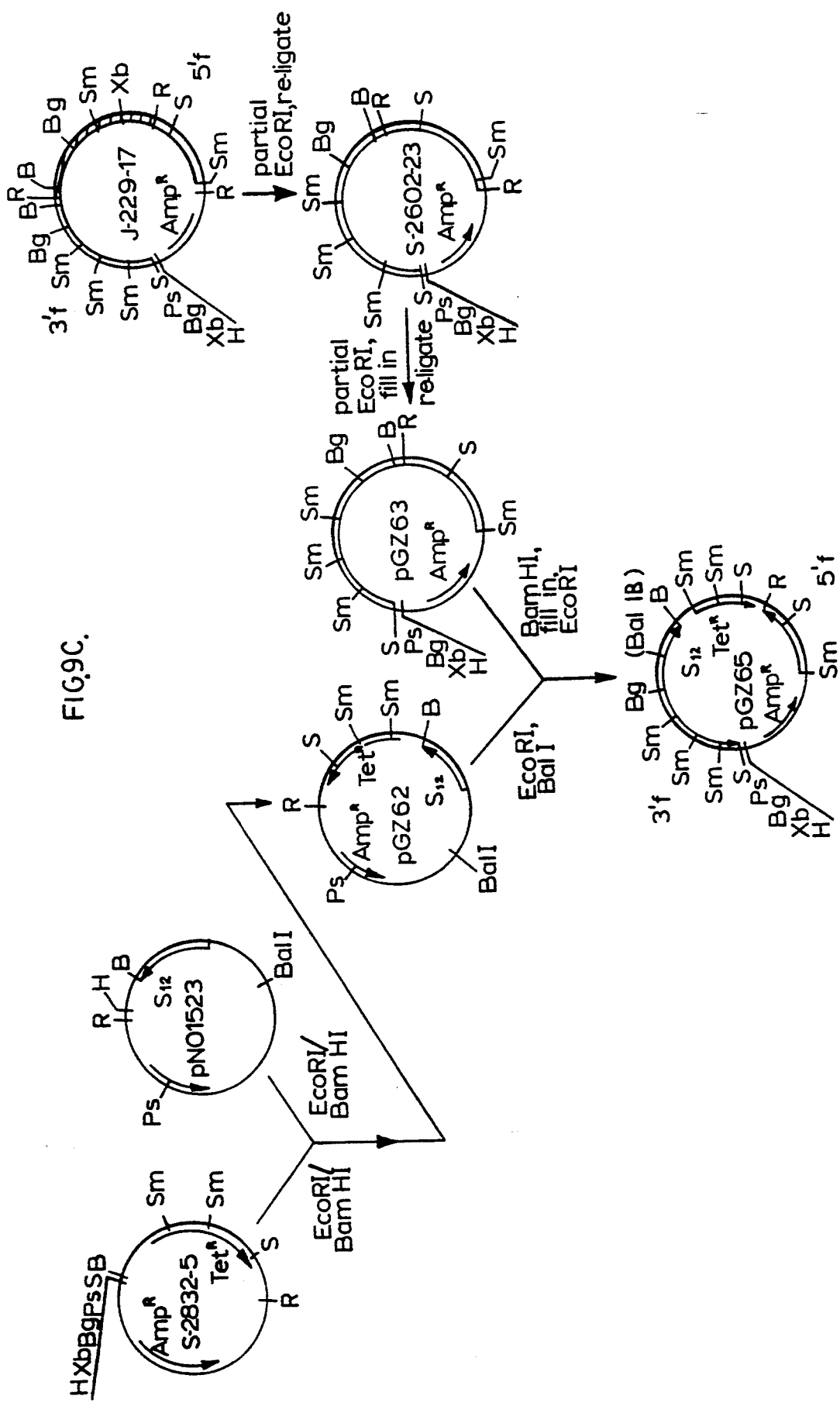

Plasmid S-2832-5 contains the Tet$^R$ gene from plasmid pRK404 and its construction is shown in FIG. 9. The Tet$^R$ gene was cloned as an EcoR I/BamH I restriction fragment into plasmid pN01523 to generate pGZ62. Plasmid pGZ63 contains the 5'- and 3'-flanking regions without any intervening DNA. The S12-Tet$^R$ gene-sandwich from pGZ62 was cloned between the flanking regions of pGZ63 to produce plasmid pGZ65. The construction of these plasmids is summarized in FIG. 9C.

3) TOX-reintegrating plasmids

Figure 10:
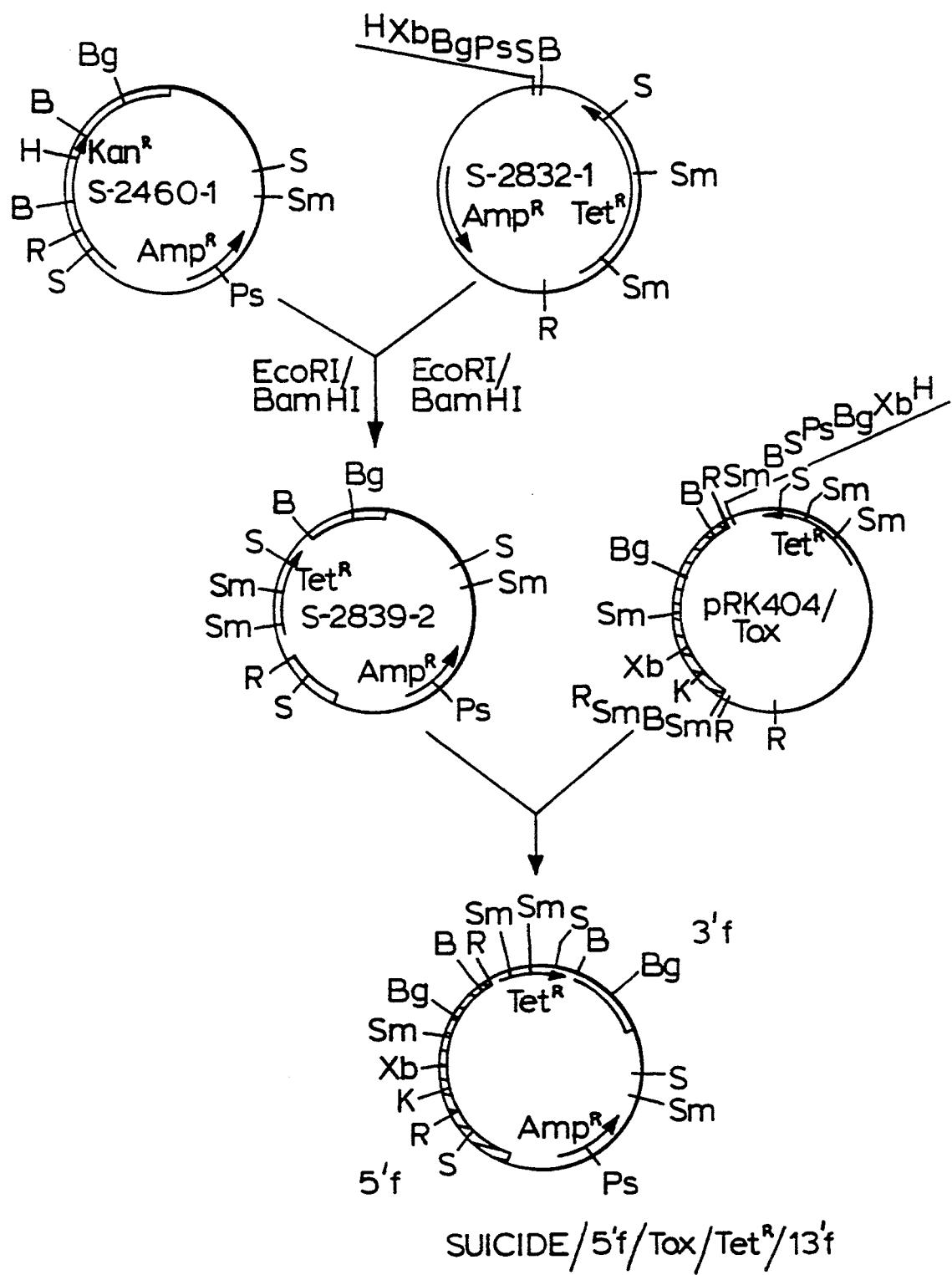
FIG. 10 shows the construction of plasmids for reintegration of TOX analogues into the B. pertussis genome by homologous recombination, the final plasmids being based on the suicide plasmid shown in FIG. 7 and containing the tetracycline resistance gene from pRK404 placed 3' to the TOX analogue gene.

To express mutated TOX genes in TOX⁻ strains of B. pertussis conjugative suicide plasmids of the type shown in FIG. 10 were constructed. They contain the TOX gene, extensive 5'- and 3'-flanking sequences and have a Tet$^R$ gene for selection cloned downstream from the TOX coding regions.

EXAMPLE XIV

This Example illustrates the deletion of the TOX gene from the B. pertussis chromosome and the reintegration of in vitro-mutated TOX genes.

1). Transformation of B. pertussis

Strains of B. pertussis were transformed by electroporation. Cells were grown in 100 ml of modified Stainer- Scholte medium to a density of about $10^9$ cells/ml, harvested in a clinical centrifuge (4000 xg for 15 min at 20° C.), washed in 25 ml of electroporation buffer (0.3M sucrose, 1 mM MgC12, 7 mM potassium phosphate, pH 7.2) and resuspended in 10 ml of the same. Plasmid DNA was added to 500 ul of the cell suspension and the mixture incubated on ice for 10 min. The cells were subjected to a single 25 kV/cm, 40 us exponential decay voltage pulse with a BTX Transfector 100, using a cuvette electrode with a 0.8 mm gap. Three ml of medium were added and the cells incubated with shaking at 37° C. for 60 min. The cells were harvested by centrifugation at 12,000 xg for 2 min, resuspended in 100 ul of medium, spread onto a Bordet-Gengou plate with antibiotic selection and incubated for 2–5 days at 37° C.

a) Deletion and replacement of the TOX operon

B. pertussis str29 is a spontaneous rpsL streptomycin resistant derivative of B. pertussis 10536. Plasmid pGZ65 contains a gene cartridge consisting of the pRK404 $Tet^R$ gene and the E. coli S12 gene cloned between the 5'- and 3'-flanking sequences of the TOX operon. This plasmid was linearized with Hind III and used to transform B. pertussis str29 to $Tet^R$, $Str^s$ resulting in the deletion of the TOX operon by homologous recombination. This TOX-deleted strain was termed 29-8 and a Southern blot analysis demonstrated the excision of the TOX allele and its replacement by the $Tc^r$, S12 gene cartridge (FIG. 13). To excise the S12-$Tet^R$ gene cartridge, strain 29-8 was subsequently transformed with linear pGZ63 plasmid DNA. Plasmid pGZ63 consists of the TOX 5'- and 3'-flanking sequences but contains no intervening DNA. Transformation with this plasmid resulted in the generation of B. pertussis 29-9 which is a streptomycin-resistant, TOX-deleted strain but contains no heterologous DNA inserted at the TOX locus. This strain was used as the host for expression of in vitro mutated TOX genes. Plasmids of the type shown in FIG. 10 contain a gene cartridge consisting of a mutated TOX gene and a $Tet^R$ gene. This gene cartridge was recombined into the B. pertussis 29-9 chromosome following introduction of the plasmid into the strain by conjugation or transformation. Expression of the TOX gene, toxicity of the PT analogues and maintenance of the S1 epitope recognised by MAb PS21 were determined as described before. The recombinant B. pertussis strains constructed and the properties of the secreted PT analogues are shown in Table 5 below.

EXAMPLE XV

This Example also illustrates the deletion of the TOX gene from the B. Pertussis chromosome and, further, illustrates the reintegration of in vitro mutated TOX genes and an analysis of the transformants.

Transformation of B. pertussis

B. pertussis 29-8 was grown in modified Stainer Scholte medium to a cell density of about $10^9$ cells/mL and harvested by centrifugation (5000 xg, 15 min., 4° C.). The cells were washed twice in 500 mL of distilled water and once in 50 mL of 10% glycerol (BRL redistilled). The cells were resuspended in a further 10 mL of 10% glycerol, aliquoted and frozen at −70° C. For transformation, 200 uL of cells were combined with 1 to 5 uL of DNA in a standard micro-cuvette and incubated on ice for 10 minutes. The cells then were subjected to a 650 V exponential decay pulse using a BTX Transfector 100 equipped with a Power Plus unit and a 0.8 mm gap electrode. One mL of modified Stainer Scholte medium was added and the cells incubated at 36° C. After 1 hour the culture was made 50 ug/mL with ampicillin and samples removed for plating onto BG plates containing streptomycin. Plates were incubated at 36° C. for 3 to 5 days.

Integration of mutant TOX alleles into strain B. pertussis 29-8

Figure 12:
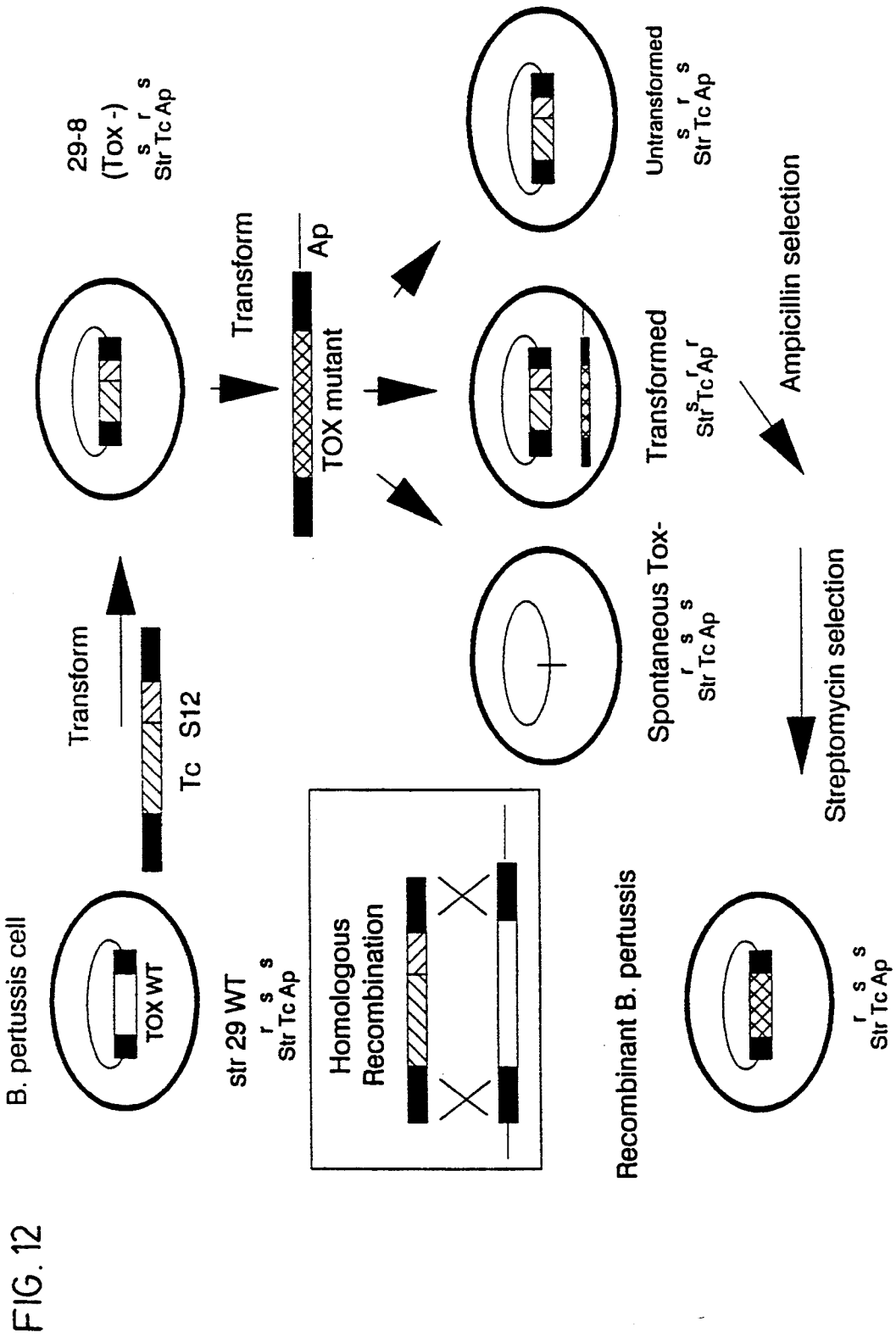
FIG. 12 shows the selective system for integration of mutant TOX allele into the chromosome of B. pertussis 29-8.

During the replacement of the $Tc^r$, S12 gene cartridge by a mutated TOX allele (FIG. 12), the cells would be expected to become $Str^r$. Initial attempts at replacement were unsuccessful due to the spontaneous excision of the $Tc^r$, S12 gene cartridge to generate $Str^r$ clones that were Tox−. This spontaneous excision event was about 10,000 times more frequent than the expected frequency of gene replacement. Directly following transformation of B. pertussis 29-8, three types of cells are obtained; namely untransformed cells which are $str^u$ and may thus be readily excluded, cells which have spontaneously excised the selectable cartridge, and transformed cells containing the non-integrated linearised plasmid. The $Ap^r$ gene, from the 5'-end of the linearised pGZ65, may be used to select against untransformed cells that have spontaneously excised the $Tc^r$, S12 gene cartridge and which are $Tc^s,Str^r,Ap^s$. Once the TOX allele is integrated by homologous recombination the $Ap^r$ gene is lost, however there is an interim period during which transformed cells are transiently resistant to ampicillin. By pre-selection of the transformants with ampicillin (50 ug/mL) for 15 to 24 hours and then imposing streptomycin selection, the frequency of spontaneous $Str^r$, Tox− clones is substantially reduced such that about 50% of putative transformants are found to be TOX+, $Tc^{r-}$, S12−. These may be selected on Bordet Gengou medium containing streptomycin and grown in liquid media to determine the secretion of PT analogue. Tox+ clones then are analyzed by colony hybridisation to confirm TOX+, $Tc^{r-}$, S12− isolates.

Plasmids based upon the original chromosomal clone J-229-17 (FIG. 8C) were constructed (FIG. 11) and termed pUC/flank/TOX. They may be linearised with Hind III and contain mutant TOX alleles sandwiched between the 5'- and 3'-flanking sequences. Transformants containing a mutant TOX allele integrated into the genome may be identified since they are $Str^r$, $Tc^s$ and secrete a PT analogue. Such analogues may be distinguished from wild-type PT because of a greatly reduced toxicity (see Table 6 below), or in the case of strain 689-169, have a new restriction site introduced by the mutation.

Analysis of recombinant B. pertussis strains

Recombinant strains of B. pertussis were demonstrated to be isogenic to B. pertussis 10536 in three ways. Firstly, the replacement, in a precise manner, of the endogenous TOX operon by the mutated allele was demonstrated by Southern blot analysis. Secondly, the kinetics of growth, antigen production and stability of the integrated TOX allele were determined. Finally, PT analogue was purified from culture supernatants for analysis.

Southern hybridisation analysis of an integrated TOX allele

The site-specific nature of the replacement of the endogenous TOX operon by the mutated Gly129 allele was demonstrated by Southern hybridisation analysis and the results are shown in FIG. 13. This analysis contains a schematic representation of the genes present at the TOX locus in B. pertussis strains 10536, wild-type (lanes 1 to 6, 12) 29-8, TOX deleted (lanes 7, 13) and 689-169, Gly129 recombinant (lanes 7 to 11, 17).

Chromosomal DNA was restricted separately with the restriction enzymes EcoR I (lanes 1, 6, 7), Bgl II (lanes 3, 9), Sal I (lanes 4, 10), Sma I (lanes 2, 8) and EcoR V (lanes 5, 11, 12, 15, 17) and probed. The fragments were separated on a 0.8% agarose gel, transferred to a Gene-screen Plus and probed with a $^{32}$p-labelled EcoR I TOX fragment that contains the entire coding sequence. The Gly129 recombinant strain (689–169) shows an identical hybridisation pattern to B. pertussis 10536, except for the appearance of a 1.0 kb fragment when the DNA is digested with the restriction endonuclease EcoR V. The replacement of the glutamic acid residue at position 129 in the S1 subunit of PT was achieved by mutation of the codon GAA codon to GGA resulting in the generation of an EcoR V restriction enzyme recognition site. This is shown by the appearance of an extra TOX specific restriction fragment (lane 11) and is indicated by an arrow in the lower panel of FIG. 13. To demonstrate the excision of the Tc$^r$,S12 selectable gene cartridge, Sal I restricted DNA was probed with nick-translated S12 and Tc$^r$ gene-specific probes. As can be seen, only chromosomal DNA isolated from B. pertussis 29-8 hybridised with these probes. From this analysis it can be seen that the Gly129 allele has been precisely integrated at the natural TOX locus and there has been no integration of heterologous DNA.

Kinetics of Growth and Antigen Production

Figure 14:
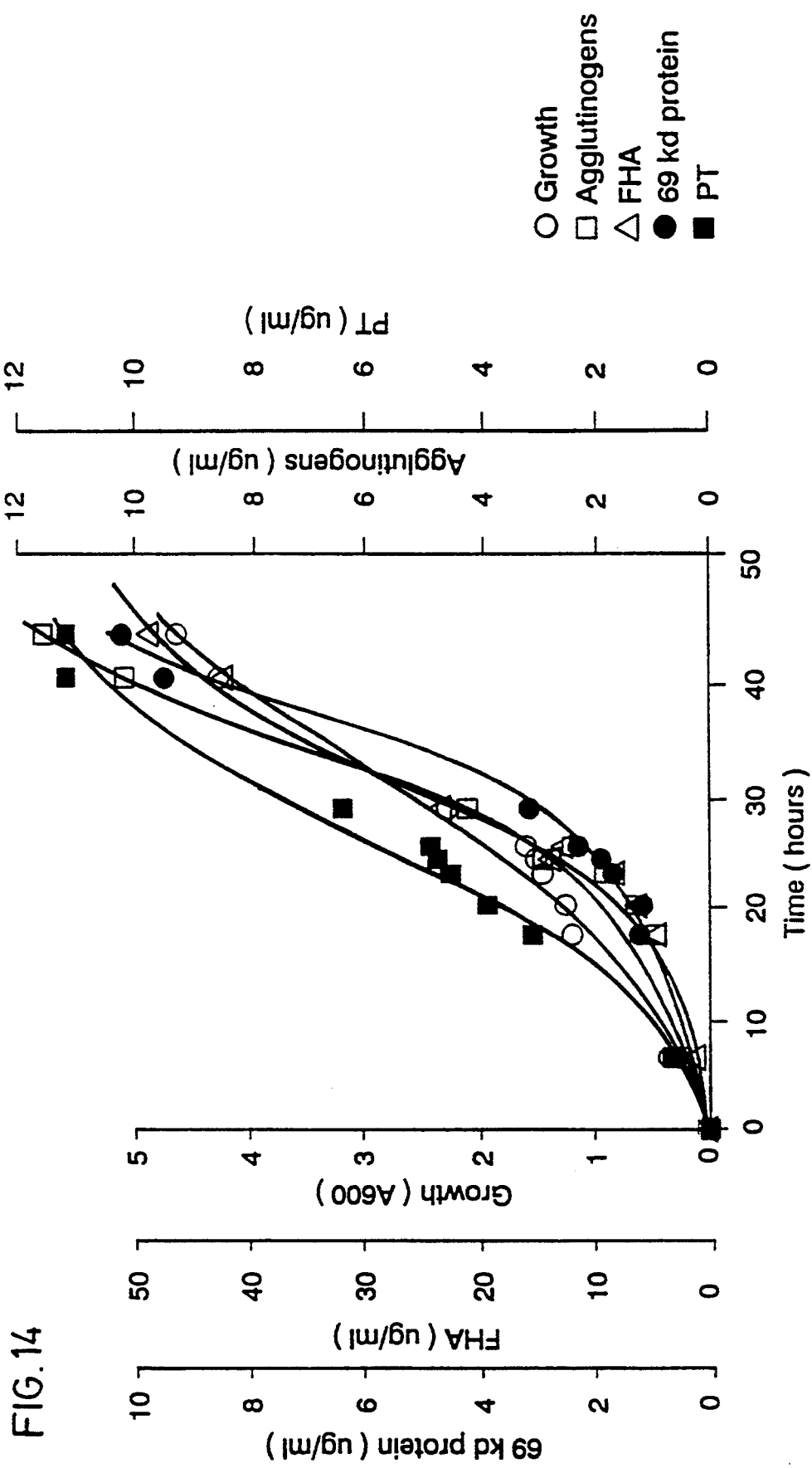
FIG. 14 shows the kinetics of antigen production by a recombinant B. pertussis strain in a 10L fermentor.

The B. pertussis Lys9Gly129 recombinant strain (989-56) was grown in modified Stainer Scholte medium in a 10L Chemap fermentor. The production of PT analogue, FHA, agglutinogens and 69KD protein were determined by specific ELISA and the results are shown in FIG. 14. The strain grew and produced the B. pertussis specific antigens with the same kinetics as the Connaught production strain B. pertussis 10536.

Stability of Re-integrated TOX alleles

The stability of TOX alleles in recombinant B. pertussis strains was determined by maintenance in a logarithmic growth phase by serial transfer for 70 generations in modified Stainer Scholte medium. At each transfer, the level of PT analogue secretion and the percentage of cells that were TOX+ were determined. There was no loss of PT expression and 100% of cells retained the TOX gene.

d) Isolation and Analysis of the Gly129 Analogue from B. pertussis 689-169

As an example of isolation of PT analogue from I culture supernatants of recombinant B. pertussis 689-169 is described. The PT analogue was purified as described in copending U.S. patent application Ser. No. 333,964 filed Apr. 6, 1989, assigned to the assignee hereof and incorporated herein by reference.

Figure 15:
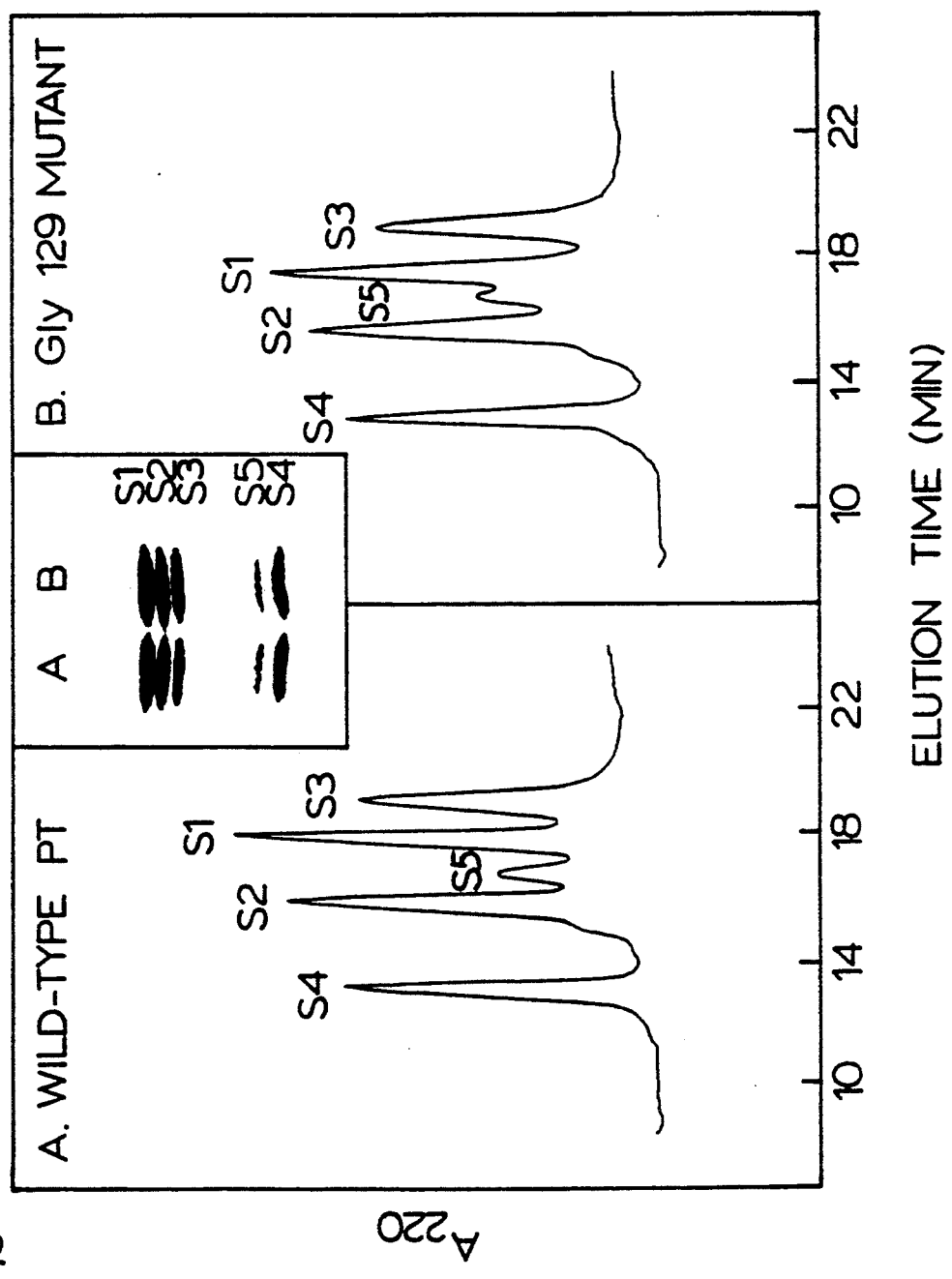
FIG. 15 shows an SDS-PAGE and a reverse phase HPLC analysis of the Gly129 PT analogue obtained from B. pertussis 689-169.

Wild-type PT is composed of five dissimilar subunits (S1 to S5). The Gly129 analogue contains all of the five protomers as shown by SDS-PAGE on a 1.5% Laemmli buffer system (lane A, wild-type PT; lane B, Gly129 analogue) and reverse phase HPLC analyses (FIG. 15) on a Vydac 214TP54 C$_4$ column. PT subunits were eluted using a linear gradient of 35 to 45% acetonitrile increasing at 0.4% per minute in 10 mM trifluoroacetic acid, with a flow rate of 0.75 ml/min. and UV detection at 220 nm.

EXAMPLE XVI

This Example describes the in vivo testing of PT mutants in mice.

PT mutants were purified from culture supernatants of recombinant Bordetella strains as indicated in Example I. These proteins were injected into mice at three different doses to test the following characteristics, according to standard procedures: acute toxicity, histamine sensitization activity and potency in the mouse intracerebral challenge test. The results are presented in Table 2 below.

To test their immunogenicity, PT analogues were injected into female BALB/C mice, 9 to 11 weeks old, at doses of 2.0, 0.5 and 0.125 ug. Mice were pre-bled and immunized on day 0. On day 23 the mice were bled again and boosted with the same immunogen, and on day 37 the mice were bled again. Blood samples (0.4 to 0.5 ml/mouse) were collected by orbital sinus bleeding and the resulting sera stored at −20° C. to await testing. Sera were assayed for their ability to neutralize PT-induced CHO cell clustering (Table 3 below), and for specific antibody responses in antigen-coat, indirect ELISA (Table 4 below). As may be seen from Tables 3 and 4 below, PT analogues are capable of inducing neutralizing antibodies and anti-PT, anti-S1 and anti-B oligomer responses.

SUMMARY OF DISCLOSURE

In summary of this disclosure, the present invention provides a novel method of detoxifying pertussis by identification of specific functional sites of pertussis toxin and production of recombinant holotoxins by site-directed mutagenesis of the toxin gene. The resulting toxin analogues are detoxified, retain an immunodominant S1 epitope, are immunogenic and are protective against the disease pertussis. Modifications are possible within the scope of this invention.

TABLE 1a

Summary of Mutations introduced into Pertussis Toxin

| Mutation Number | Mutation | Clone No. |
|---|---|---|
| 1. | ARG$^9$ → Δ9 | S-2679-1-11 |
| 2. | ARG$^9$ → GLU$^9$ | S-2815-1-8 |
| 3. | ARG$^9$ → LYS$^9$ | S-2953-21 |
| 4. | ARG$^9$ → HIS$^9$ | S-3046-4 |
| 5. | ARG$^{13}$ → Δ13 | S-2679-2-1 |
| 6. | ARG$^{13}$ → GLU$^{13}$ | S-2779-2-1 |
| 7. | ARG$^9$–ARG$^{13}$ → Δ9–13 | S-2829-2-19 |
| 8. | ARG$^9$ ARG$^{13}$ → GLU$^9$ GLU$^{13}$ | S-2779-3-2 |
| 9. | ARG$^{58}$ → GLU$^{58}$ | J-444-2-2 |
| 10. | ARG$^{57}$ ARG$^{58}$ → Δ57Δ58 | J-482-11 |
| 11. | TYR$^{26}$ → ALA$^{26}$ | S-3123-2 |
| 12. | TYR$^{26}$ → CYS$^{26}$ | S-3140-22 |
| 13. | CYS$^{41}$ → ALA$^{41}$ | S-2515-5-10 |
| 14. | CYS$^{41}$ → SER$^{41}$ | S-3124-6 |

TABLE 1a-continued

Summary of Mutations introduced into Pertussis Toxin

| Mutation Number | Mutation | Clone No. |
|---|---|

TABLE 1b-continued

In vitro characterization of pertussis toxin analogues obtained from recombinant *B. paravertussis*.

| Mutation Number | Residual Toxicity | ADPR Activity | S1 Epitope |
|---|---|---|---|
| 15. | 0.2 | 0.1 | — |
| 16. | 0.1 | ND | ++ |
| 17. | 0.1 | 0.3 | ++++ |
| 18. | 0.02 | 0.1 | +/− |
| 19. | 0.7 | 2.5 | ++ |
| 20. | 0.1 | 0.3 | ++ |
| 21. | 0.3 | 0.2 | — |
| 22. | 0.1 | ND | — |
| 23. | 0.2 | ND | — |
| 24. | 0.2 | ND | + |
| 25. | 0.4 | ND | — |
| 26. | 0.1 | 0.3 | ++++ |
| 27. | 0.02 | 0.1 | +/− |
| 28. | 0.2 | 0.1 | — |
| 29. | 12.0 | ND | ++++ |
| 30. | 0.2 | 0.6 | — |
| 31. | 0.4 | ND | — |
| 32. | 1.0 | ND | ++++ |
| 33. | 100 | ND | ++++++ |
| 34. | 50 | 100 | ++++ |
| 35. | 20 | ND | ++++ |
| 36. | 0.2 | 0.1 | — |
| 37. | 0.1 | 0.1 | — |
| 38. | 0.1 | 0.1 | — |
| 39. | 0.1 | ND | — |
| 40. | 0.1 | ND | — |
| 41. | 0.2 | ND | — |
| 42. | 0.5 | ND | — |
| 43. | 3.0 | ND | — |
| 44. | 0.3 | ND | — |
| 45. | 0.4 | ND | — |
| 46. | 0.2 | 0.1 | — |
| 47. | 0.5 | ND | — |
| 48. | 0.4 | 0.3 | — |
| 49. | 0.2 | 0.1 | ++++ |
| 50. | 100 | 100 | ++++ |
| 51. | 14.0 | | +++++ |
| 52. | 35.0 | | +++++ |
| 53. | 13.0 | | +++++ |
| 54. | 0.2 | | ++ |
| 55. | 0.6 | | +++++ |
| 56. | 29.0 | | ++++ |
| 57. | 0.1 | | ++ |
| 58. | <0.01 | <0.01 | +++ |
| 59. | 0.1 | | + |
| 60. | 12.0 | | +++++ |
| 61. | 100.0 | | +++++ |
| 62. | 0.03 | 0.2 | +++ |
| 63. | 0.1 | | + |
| 64. | 0.1 | | +++ |
| 65. | 0.1 | | + |
| 66. | 10.0 | | + |

Residual toxicity is the ratio of the apparent PT concentration determined by the CHO cell clustering assay to the actual concentration of PT mutant determined by ELISA expressed as a percentage.
ADPR activity is the extent of ADP-ribosylation of bovine transducin catalysed by a PT analogue, relative to that catalysed by an equal concentration of wild-type PT, expressed as a percentage.
S1 epitope refers to the expression of an immunodominant S1 epitope recognized by a specific monoclonal antibody PS21, as compared with the wild-type PT (++++).
ND denotes not determined.

TABLE 2

Biological Activity of PT mutants in mice

| Analogue | Acute Toxicity $LD_{50}$ (μg) | HS Activity $LD_{50}$ (μg) | M.P.T. $ED_{50}$ (μg) |
|---|---|---|---|
| Native | ~2 | ~0.2 | ≈2 |
| $GLY^{129}$ | >5 | ~3 | ~2 |
| $GLN^{29}$ | >16 | >3 | 16 |
| $ASN^{29}$ | >5 | ~3 | 1.5 |
| $GLU^{58}$ | >5 | 1.5 | 8.5 |
| LYS9 | 0 | 6 | 2 |
| $GLY^{129}$ (S3)$ASN^{92}$ $ARG^{93}$ | >20 | 7 | 2 |
| (S3)ASN92 ARG93 | 3 | 0.4 | ≧2 |
| *HIS9 | | 5 | 4 |
| *LYS9GLY129 | | >>40 | 4–5 |
| *GLY129/S3(91–93) | | >20 | 2–3 |
| *GLY129 | | ~6 | ~3 |
| *ASN129 | | 3 | ND |

*Indicates PT analogue derived from *B. pertussis*
HS Activity denotes histamine sensitizing activity.
M.P.T. denotes mouse intracerebral challenge protection test.
$LD^{50}$ is the dose resulting in death of 50% of the test animals.
$ED^{50}$ is the dose resulting in protection of 50% of the test animals.
Native denotes PT from *B. pertussis* 10536.

TABLE 3

Neutralizing effect of immune sera on PT-induced CHO cell clustering

| Analogue Dose (μg) | Pre-bleed | Post-1 bleed | Post-2 bleed |
|---|---|---|---|
| $GLY^{129}$ | | | |
| 2.0 | <2 | <2 | 256 |
| 0.5 | <2 | <2 | 128 |
| 0.125 | <2 | <2 | 64 |
| $GLN^{129}$ | | | |
| 2.0 | <2 | <2 | 128 |
| 0.5 | <2 | <2 | 256 |
| 0.125 | <2 | <2 | 128 |
| $ASN^{129}$ | | | |
| 2.0 | <2 | <2 | 512 |
| 0.5 | <2 | <2 | 128 |
| 0.125 | <2 | <2 | 256 |
| Saline | <2 | <2 | <2 |

Mice were pre-bled and immunized on day 0. On day 23 they were bled again (post-1 bleed) and boosted. Final sera were obtained on day 37 (post-2 bleed).
The neutralizing ability of the sera is expressed as the maximum dilution at which CHO cell clustering was inhibited.

TABLE 4

Specific antibody titres of immune sera

| Analoge Dose (μg) | Pre-bleed | | | Post-1 bleed | | | Post-2 bleed | | |
|---|---|---|---|---|---|---|---|---|---|
| | PT | S1 | B | PT | S1 | B | PT | S1 | B |
| $GLY^{129}$ | | | | | | | | | |
| 2.0 | NR | NR | NR | 63 | 2 | 50 | 500 | 80 | 200 |
| 0.5 | NR | NR | NR | 13 | 1 | 8 | 160 | 32 | 56 |
| 0.125 | NR | NR | NR | 10 | 0.5 | 8 | 200 | 32 | 80 |
| $GLN^{129}$ | | | | | | | | | |
| 2.0 | NR | NR | NR | 22 | 0.7 | 20 | 200 | 40 | 125 |
| 0.5 | NR | NR | NR | 8 | 0.5 | 6 | 200 | 40 | 100 |
| 0.125 | NR | NR | NR | 5 | <0.5 | 2 | 125 | 20 | 50 |

TABLE 4-continued

| Analoge Dose (μg) | Specific antibody titres of immune sera | | | | | | | | |
|---|---|---|---|---|---|---|---|---|---|
| | Pre-bleed | | | Post-1 bleed | | | Post-2 bleed | | |
| | PT | S1 | B | PT | S1 | B | PT | S1 | B |
| ASN$^{129}$ | | | | | | | | | |
| 2.0 | NR | NR | NR | 40 | 1 | 40 | 500 | 140 | 280 |
| 0.5 | NR | NR | NR | 7 | <0.5 | 3 | 316 | 22 | 80 |
| 0.125 | NR | NR | NR | 7 | <0.5 | 4 | 180 | 63 | 125 |
| Saline | NR | NR | NR | NR | NR | NR | NR | NR | NR |

Immunization and bleeding were performed as described in Table 3.
Antigens used were PT holotoxin, isolated S1 subunit and isolated B oligomer.
The units are the dilution factor divided by 1000 giving an ELISA absorbance value equal to twice the background.
NR denotes not reactive with antigen.

TABLE 5

In vitro characterization of pertussis toxin analogues from recombinant *B. pertussis*

| Mutation Number | Clone | Residual Toxicity | ADPR Activity | S1 Epitope |
|---|---|---|---|---|
| 9 | S-3036-2 | 0.2 | 0.3 | +++ |
| 13 | S-3122-3-1 | 0.1 | ND | ND |
| 26 | S-2962-1-2 | 0.2 | ND | ND |
| 27 | S-2962-2-1 | 0.1 | ND | ND |
| 34 | S-3122-1-3 | 50 | ND | +++++ |
| 49 | S-3122-2-3 | 0.1 | ND | +++ |
| 50 | S-3006-3 | 100 | 100 | ++++ |

All terms are as defined in Tables 1a and 1b.
ND denotes not determined.

TABLE 6

In Vitro characterization of PT Analogues obtained from strains of recombinant *B. pertussis* which do not contain a selectable antibiotic resistance gene.

| Mutation Number | Clone | Strain | Residual Toxicity | ADPRT Activity |
|---|---|---|---|---|
| 16 | S-3394-12 | 789-94 | 0.1 | ND |
| 17 | S-3319-3-9 | 689-169 | 0.2 | 0.2 |
| 20 | S-3484-2-27 | 989-99 | 0.3 | 0.6 |
| 21 | S-3346-3-24 | 689-71 | 0.1 | ND |
| 26 | S-3346-1-12 | 689-40 | 0.1 | ND |
| 27 | S-3346-2-44 | 689-197 | 0.1 | ND |
| 58 | S-3484-3-27 | 989-56 | <0.0005 | <0.0001 |
| 62 | S-3453-18 | 889-48 | 0.03 | 0.2 |

What we claim is:

1. A strain of *Bordetella pertussis* in which the toxin operon has been replaced by a mutant gene formed by site-directed mutagenesis of a nucleotide sequence coding for at least one specific amino acid residue in the S1 and for S3 subunit of pertussis holotoxin responsible for pertussis toxin toxicity and having ATCC accession number 53833, 53834, 53835, 53836, 53837, 53974, 53975 or 53976.

2. A method for the production of immunoprotective genetically detoxified mutant of pertussis holotoxin, which comprises:
   identifying at least one amino acid residue in at least one of the S1, S2 and S3 subunit of the holotoxin which confers toxicity to the toxin,
   effecting site-directed mutagenesis of the holotoxin gene to remove or replace a nucleotide sequence coding for said at least one such residue and produce a mutated holotoxin operon for the
   substituting the mutated holotoxin operon, native gene in a Bordetella organism which is selected from the group consisting of *B. pertussis, B. parapertussis, B. bronchiseptica* and *B. avium*, and
   growing the transformed organisms to produce immunoprotective, genetically-detoxified holotoxin.

3. The method of claim 2 wherein said at least one amino acid residue is identified as a single functionally-active amino acid in the S1 subunit of the holotoxin, and said mutagenesis is effected at said single amino acid.

4. The method of claim 2 wherein said single amino acid is ARG$^9$, GLU$^{129}$ or ARG$^{58}$ and are replaced by LYS$^9$, GLY$^{129}$ or GLU$^{58}$ respectively.

5. The method of claim 2 wherein said at least one amino acid residue is identified as multiple functionally-active amino acids of the holotoxin, and said mutagenesis is effected at each said amino acid.

6. The mthod of claim 5 wherein said multiple amino acids comprise GLU$^{129}$TYR$^{130}$ or GLU$^{129}$/(S3)TYR$^9$-2LYS$^{93}$, ARG$^{58}$ GLU$^{129}$, ARG$^9$ GLU$^{129}$, ARG$^9$ ARG$^{58}$ GLU$^{129}$, (S1) ARG$^{58}$ GLU$^{129}$/(S3) 91 to 93 or (S1) ARG$^9$ GLU$^{129}$/(S3) 91 to 93 and are replaced by GLY$^{129}$ PHE$^{130}$, GLY$^{129}$/(S3) ASN92 ARG$^{93}$, GLU$^{58}$ GLY$^{129}$, LYS$^9$ GLY$^{129}$, LYS$^9$ GLU$^{58}$ GLY$^{129}$, (S1) GLU$^{58}$ GLY129/(S3) 91 to 93 delete and (S1) LYS$^9$ GLY$^{129}$/(S3) 91 to 93 delete, respectively.

7. The method of claim 2 wherein said substitution step is effected by conjugation or by high voltage electroporation.

8. The method of claim 2 including killing said grown transformed organism and formulating the killed organism as a whole cell vaccine.

* * * * *

UNITED STATES PATENT AND TRADEMARK OFFICE
CERTIFICATE OF CORRECTION

PATENT NO. : 5,358,868
DATED : Oct. 25, 1994
INVENTOR(S) : M. H. Klein et al.

It is certified that error appears in the above-identified patent and that said Letters Patent is hereby corrected as shown below:

Col. 27, line 54, change "and for" to read --and/or--

Col. 28, line 24, change "operon for the" to read --operon,--

Col. 28, line 25, change "operon, native" to read --operon for the native--.

Col. 28, line 29, change "organisms" to --organism--.

Signed and Sealed this

Second Day of December, 1997

*Attest:*

BRUCE LEHMAN

*Attesting Officer*   Commissioner of Patents and Trademarks

Disclaimer 5,358,868 - Michel H. Klein, Willowdale; Heather A. Boux, Aurora; Stephen A. Cockle, Richmond Hill; Sheena M. Loosmore, Aurora; Gavin R. Zealey, Concord, all of Canada. Patent dated Octoeber 25, 1994. Disclaimer filed November 23, 1998, by the assignee, Connaught Laboratories Limited.

Hereby enters this disclaimer to claims 1 and 6 of said patent.
*(Official Gazette,* July 27, 1999)